United States Patent [19]

Ducheyne et al.

[11] Patent Number: 5,817,327

[45] Date of Patent: Oct. 6, 1998

[54] INCORPORATION OF BIOLOGICALLY ACTIVE MOLECULES INTO BIOACTIVE GLASSES

[75] Inventors: Paul Ducheyne, Rosemont, Pa.; Shulamith Radin, Voorhees, N.J.; Erick Manuel Santos, Philadelphia, Pa.

[73] Assignee: The Trustees of the University of Pennsylvania, Philadelphia, Pa.

[21] Appl. No.: 459,001

[22] Filed: Jun. 2, 1995

Related U.S. Application Data

[60] Division of Ser. No. 406,047, Mar. 17, 1995, abandoned, which is a continuation-in-part of Ser. No. 281,055, Jul. 27, 1994, abandoned.

[51] Int. Cl.$^6$ ............................. A61F 2/28; A61K 31/695
[52] U.S. Cl. ........................ 424/425; 424/422; 424/484; 514/965; 523/11; 523/16
[58] Field of Search ..................................... 424/422, 425, 424/426, 484; 501/53, 39; 623/11, 16; 514/965

[56] References Cited

U.S. PATENT DOCUMENTS

| | | | |
|---|---|---|---|
| 4,563,350 | 1/1986 | Nathan et al. | 424/95 |
| 4,772,203 | 9/1988 | Scheunemann | 433/173 |
| 4,775,646 | 10/1988 | Hench et al. | 502/2 |
| 4,849,378 | 7/1989 | Hench et al. | 501/12 |
| 4,851,150 | 7/1989 | Hench et al. | 252/315.6 |
| 4,859,525 | 8/1989 | Hench et al. | 428/260 |
| 4,869,906 | 9/1989 | Dingeldein et al. | 424/423 |
| 4,976,736 | 12/1990 | White et al. | 623/16 |
| 5,074,916 | 12/1991 | Hench et al. | 106/35 |
| 5,108,436 | 4/1992 | Chu et al. | 623/66 |
| 5,200,334 | 4/1993 | Dunn et al. | 435/182 |
| 5,204,106 | 4/1993 | Schepers et al. | 424/423 |
| 5,207,710 | 5/1993 | Chu et al. | 623/16 |
| 5,270,300 | 12/1993 | Hunziker | 514/12 |
| 5,344,654 | 9/1994 | Rueger et al. | 424/423 |
| 5,356,635 | 10/1994 | Raman et al. | 424/484 |
| 5,374,427 | 12/1994 | Stille et al. | 424/423 |
| 5,702,717 | 12/1997 | Cha et al. | 424/425 |
| 5,711,958 | 1/1998 | Cohn et al. | 424/423 |

FOREIGN PATENT DOCUMENTS

| | | |
|---|---|---|
| 0 462 608 A1 | 6/1991 | European Pat. Off. . |
| 0 616 814 a1 | 3/1994 | European Pat. Off. . |
| 0616814 A1 | 3/1994 | European Pat. Off. . |
| 31 34728 A1 | 9/1981 | Germany . |
| Nr 222498 | 5/1985 | Germany . |
| Nr 248351 | 5/1987 | Germany . |
| 3905394 | 9/1989 | Germany . |
| 5253286 | 5/1993 | Japan . |
| 05253286 | 10/1993 | Japan . |
| 1542414 | 3/1979 | United Kingdom . |
| 2 255 907 | 11/1992 | United Kingdom . |
| WO 92/07554 | 5/1992 | WIPO . |
| WO 93/05823 | 4/1993 | WIPO . |

OTHER PUBLICATIONS

*American Academy of Orthopaedic Surgeons*, 1993, Bone Formation and Bone Regeneration. Tampa, FL: ).

Andersson et al., "Calcium Phosphate Formation at the Surface of Bioactive Glass in vitro", *J. Biomed Mater. Res.* 25:1019–1030 (1991).

Andersson et al., "On the Bioactivity of Silicate Glass", *J. Non–Cryst Solids* 129:145–151 (1991).

Avnir et al., "Encapsulation of Organic Molecules and Enzymes in Sol–Gel Glasses", *American Chemical Society*, Ch. 27, pp. 385–404 (1992).

Beck et al., *J. Bone Miner. Res.* 6(9):961 (1991).

Boone et al., "Bone Attachment to Hydroxyapatite Coated Polymers", *J. Biomed Mater. Res.* 23(A2):183–199 (1989).

(List continued on next page.)

*Primary Examiner*—Robert H. Harrison
*Attorney, Agent, or Firm*—Woodcock Washburn Kurtz Mackiewicz & Norris, LLP

[57] ABSTRACT

Carriers comprising silica-based glass providing for the controlled release of biologically active molecules, their methods of preparation, and methods of use are disclosed. The carriers are prepared using a sol-gel-derived process. Biologically active molecules are incorporated within the matrix of the glass during production.

4 Claims, 15 Drawing Sheets

OTHER PUBLICATIONS

Braun et al., "Biocatalysis by Sol–Gel Entrapped Enzymes", *J. of Non–Crystalline Solids,* 147 and 148:739–743 (1992).

Braun et al., "Biochemically Active Sol–Gel Glasses —The Trapping of Enzymes", *Materials Letters* 10:1–5 (1990).

Canalis et al., "Systemic and Local Factors and the Maintenance of Bone Quality", *Calcified Tissue Int.* 53:S90–s93 (1993).

Canalis et al., "Insulin Like Growth Factors Decrease Collagen Degradation and Collagenase Expression in Bone Cultures", *J. Bone Miner. Res.* 8:S237 (1993).

Chesmel et al., "TGF–β Enhances Osseointegration In Vivo", *Bioceramics,* 6:21–25 (1993).

Cornell and Lane, "Newest Factors in Fracture Healing", *Clin. Orthop.* 277:297–311 (1992).

Cornell et al., "Treatment of Experimental Osteomyelitis with Antibiotic–Impregnated Bone Graft Substitute", *J. of Orthopaedic Research,* 11(5):619–626 (1993).

Damen and Ten Cate, "The Effect of Silicic Acid on Calcium Phosphate Precipitation", *J. Dental Res.* 68(9):1355–1359 (1989).

Damien and Parsons, "Bone Graft and Bone Substitutes: A Review of Current Technology and Applications", *J. Applied Biomater.* 2:187–208 (1991).

Downes et al., "Growth–Hormone Loaded Bioactive Ceramics", *J. Mater. Sci.:Mater. Med.,* 2:176–180 (1991).

Ducheyne P., "Bioceramics: Material Characteristics Versus In Vivo Behavior", *J. Biomed. Mater. Res.* 21(A2):219–236 (1987).

Ducheyne and Cuckler, "Bioactive Ceramic Prosthetic Coatings", *Clin. Orthop. Rel. Res.* 76:102–114 (1992).

Ellerby et al., "Encapsulation of Proteins in Transparent Porous Silicate Glasses Prepared by the Sol–Gel Method", *Science* 255:1113–1115 (1992).

Friedman et al., "In Vivo Mechanical and Histological Evaluation of Bone in Growth and Apposition in the Rabbit Female".

Gerhart et al., "Healing Segmental Femoral Defects in Sheep Using Recombinant Human Bone Morphogenetic Protein", *Clin. Orthop.* 293:317–326 (1993).

Gombotz et al., "Stimulation of Bone Healing by Transforming Growth Factor–Beta Released from Polymeric", *J. App. Biomat.,* 5:141–150 (1994).

Gunasekaran et al., "Mineralized Collagen As A Substitute for Autograft Bone that can Deliver Bone Morphogenic Protein", 19th Annual Meeting of the *Society for Biomaterials,* p. 258 (1993).

Hench, L.L., "Bioceramics and the Origin of Life" *J. Biomed Mater. Res.* 23:685–703 (1989).

Hench, L.L., "Bioactive Ceramics", *Ann. N. Y. Acad. Sci.* 523:54–71 (1988).

Hench, L.L., "Bioceramics: from Concept to Clinic", *J. Am. Ceram. Soc.* 74(7):1487–1510 (1991).

Hock et al., "Insulin–Like Growth Factor I Has Independent Effects on bone Matrix Formation and Cell Replication", *Endocrinology* 122(1):254–260 (1988).

Johnson et al., "Resistant Nonunions and Partial or Complete Segmental Defects of Long Bones", *Clin. Orthop.* 277:229–237 (1992).

Johnson et al., "Bone Morphogenetic Protein augmentation Grafting of Resistant Femoral Nonunions", *Clin. Orthop.* 230:257–265 (1988).

Johnson et al., "Repair of Segmental Defects of the Tibia with Cancellous Bone Grafts Augmented with Human Bone Morphogenetic", *Clin. Orthop.* 236:249–257 (1988).

Johnson et al., "Distal Metaphyseal Tibial Nonunion. Deformity and Bone Loss Treated by Open Reduction, Internal Fixation, and Human Bone Morphogenetic Protein (hBMP)", *Clin. Orthop.* (1990).

Joyce et al., "Transforming Growth Factor–β in the Regulation of Fracture Repair", *Orthop Clin. North am.* 21(1):199–209 (1990).

Joyce et al., "Transforming Growth Factor–β and the Initiation of Chondrogenesis and Osteogenesis in the Rat Femur", *J. Cell Biol.* 110(6):2195–2207 (1990).

Kokubo, T., "Bioactive Glass Ceramics: Properties and Applications", *Biomaterials* 12(2):155–163 (1991).

Li et al., "Effects of Ions in Aqueous Media on Hydroxyapatite Induction by Silica Gels and its Relevance to Bioactivity of Bioactive Glasses and Glass–Ceramics", *J. Appl. Biomater.,* 4:221–229 (1993).

Li et al., "Apatite Formation Induced by Silica in a Stimulated Body Fluid", *J. Amer. Ceram. Soc.,* 75:2094–2097 (1993).

Li et al., "An Investigation of Bioactive Glass Powders by Sol–Gel", *J. Applied Biomater* 2:231–239 (1991).

Liu et al., "Development Characterization of a New–Type Bioactive Glass–Ceramic", *Annual Meeting of the Society For Biomaterials,* p. 5 (1993).

Lucas et al., "Ectopic Induction of Cartilage and Bone By Water–Soluble Proteins From Bovine Bone Using a Collagenous Delivery Vehicle", *J. Biomed Mater. Res.*

McCarthy et al., "Regulatory Effects of Insulin–Like Growth Factors I and II on Bone Collagen Synthesis in Rat Calvarial Cultures", *Endocrinology* 124(1):301–309.

Meikle et al., "Effect of Poly DL–Lactide–Co–Glycolide Implants and Xenogeneic Bone Matrix–Derived Growth Factors on Calvarial Bone Repair in the Rabit", *Biomaterials* 15(7):513–521 (1994).

Miclau et al., "In Vitro Pharmacokinetics of Antibiotic Release from Locally Implantable Materials", *J. of Orthopaedic Research,* 11:627–632 (1993).

Olmedo et al., "Intramedullary TGF–β Administration and Osteogenesis in an In Vivo Rat Model", *19th Annual Meeting of the Society for Biomaterials,* p. 6 (1993).

Otsuka et al., "A Novel Skeletal Drug Delivery System for Antibiotic Drugs Using Self–Setting Bioactive Bone Cement Based on $CaO$–$SiO_2$–$P_2O_5$ Glass", In: Yamamuro T, Kokubo T, Nakamura, T, eds. *Bioceramics* 5 5th ed. Kyoto, 241–248 (1992).

Pereira et al., "Calcium Phosphate Formation on Sol–Gel–derived Bioactive Glasses In Vitro", *J. of Biomed. Mat. Res.,* 28:693–698 (1994).

Radin et al., "The Effect of Calcium Phosphate Ceramic Composition and Structure on In Vitro Behavior. II. Precipitation", *J. Biomed Mater. Res.* 27:35–45 (1993).

Rawlings, R.D., "Composition Dependence of the Bioactivity of Glassed", *J. Mater. Sci. Letters* 11:1340–1343 (1992).

Sampath et al., BMP–7 *J. Biol. Chem.* 267(28):20352 (1992).

Schepers et al., "Bioactive Glass Particulate Material as a Filler for Bone Lesions", *J. Oral Rehabil.* 18:439–452 (1991).

Silbermann, M., "In Vitro Systems for Inducers of Cartilage and Bone Development", *Biomaterials,* 11:47–49 (1990).

Stoscheck et al., "Integrated Separation Systems", *Anal. Biochem.,* 160:301–305 (1987).

Tashijian, Jr. et al., "Platelet–Derived Growth Factor Stimulates Bone Resorption Via a Prostaglandin–Mediated Mechanism", *Endocrinology* 111:118–124 (1982).

Urist, M.R., "Bone: Formation by Autoinduction", *Science* 150:893–899 (1965).

Wozney, J.M., *Prog. Growth Factor Res.* 1(4):267 (1989).

Wozney et al., "Novel Regulators of Bone Formation: Molecular Clones and Activities", *Science* 242:1528–1534 (1988).

Yamanaka et al., "Enzymatic Activity of Glucose Oxidase Encapsulated in Transparent Glass by the Sol–Gel Method", *Chemistry of Materials,* 4(3):495–497 (1992).

Yasko et al., *J. Bone Joint Surg.* 74(7):1111 (1992).

Yasko et al., *J. Bone Joint. Surg.* 74(5):659 (1992).

Younger et al., *Clin. Orth. Rel. Res.* (1992) 277:297–311.

Campbell, et al., 40th Annual Meeting Orthopaedic Research Society, p. 775, Feb. 21–24, 1994.

Otsuka, et al., Drug release from a novel self–setting Bioactive Glass Bone Cement . . . , *J. of Biomedical Materials Research,* vol. 29:33–38 (1995).

Quantachrome Corp. , Excerpts from Autosorb–1 Manual, pp. II–4–6.

Drake et al., "The Use of Controlled–Release Glass for Controlled Delivery of Bioactive Material", Biochem. Soc. Trans., 1985, 13/2, pp. 516–520.

Otsuka et al., "A Novel Skeletal Drug Delivery System for Antiobiotic Drugs Using Self–Setting Bioactive Bone Cement Based on $CaO$–$SiO_2$–$P_2O_5$ Glass", Bioceramics vol. 5, pp. 241–248, 1992.

INCORPORATION OF BIOLOGICALLY ACTIVE MOLECULES INTO BIOACTIVE GLASSES

This is a division of application Ser. No. 08/406,047, filed Mar. 17, 1995, abandoned, which is a continuation-in-part of Ser. No. 08/281,055, filed Jul. 27, 1994, abandoned.

FIELD OF THE INVENTION

The present invention relates to the incorporation of biologically active molecules into the matrix of glass, in particular bioactive glass, using a sol-gel-derived process of production.

BACKGROUND OF THE INVENTION

Musculoskeletal injuries have a substantial impact on the health and quality of life of millions of Americans. Delayed healing of and non-unions of fractures represent a continuous orthopaedic challenge. The conventional way of treating these problems is to use bone plates or screws in combination with autologous bone grafting.

As a natural composite material, autogenous bone graft has been shown to have both osteoconductive and osteoinductive properties. In addition, it is a sterile, non-immunogenic and non-toxic material, which has the ability to be fully incorporated into the fracture site. Notwithstanding the long duration for their activity to develop, autogenous bone grafts are the gold standard by which synthetic composites are compared. Given that there is also a limited supply and harvest site morbidity of autogenous bone graft material, there is significant motivation to develop synthetic composites. To date, no synthetic bone graft substitutes have fully achieved the properties of autogenous bone graft.

Enhancing the rate and probability of fracture healing and the promotion of bone formation and healing of delayed and non-union fractures are of great clinical significance. (NIH/AAOS sponsored workshop. Bone Formation and Bone Regeneration. Tampa, Fla.: *American Academy of Orthopaedic Surgeons,* 1993). The large population of patients with delayed unions and non-unions of bone, the large direct medical costs, and the societal costs related to their long term disability, highlight the need for effective and improved methods of treatment.

Advances in materials science and the identification of osteogenic and osteoinductive growth factors have invited the investigation of newer alternatives for autogenous bone grafting. osteogenesis, which is the process of bone formation, involves both osteoconduction and osteoinduction. Osteoconduction is the process in which differentiated bone-forming cells produce a bone matrix upon an existing substrate. Materials that promote this process are considered osteoconductive. Osteoinduction is the process by which undifferentiated mesenchymal precursor cells are transformed into differentiated bone forming cells. Factors or materials that promote this process are considered to be osteoinductive.

Growth factors delivered by biologically active controlled release carriers have the potential for improved fracture healing and lower morbidity, thereby resulting in improved patient care and a decrease in the overall costs associated with fracture care. Similarly, the delivery of antibiotics by such carriers, either alone or in addition to growth factors, will help reduce the incidence of infections, which can further contribute to delays in healing. In fractures involving, for example, the spine, the incorporation of anti-inflammatory agents and analgesics will help control inflammation, which can also delay the healing process, and contribute to patient comfort during the healing process. Additionally, the controlled release of such materials regardless of the bioactivity of the carrier would represent a distinct advantage over current delivery methods and assist fixation of implants.

The ideal synthetic graft would be a scaffolding material that would stimulate bone tissue to grow in place of the scaffold as it degrades. (Damien et al., *J. Applied Biomater.* (1991) 2:187–20.) Synthetic materials intended as bone graft substitutes should have mechanical and other properties similar to those of bone, and should be biocompatible with the surrounding tissues. In order to provide a union across the fracture site they must serve not only as scaffolding materials but also, similarly to native bone, have a stimulatory effect on bone tissue regeneration.

The currently used synthetic bone graft materials are considered osteoconductive in that they elicit the formation of the bone matrix at their surfaces. Furthermore, they lead to a contiguous interface with bone or are replaced by bone tissue. Such properties suggest a chemical interaction between these bioactive materials and the bone environment. Cells existing in the bone matrix environment exhibit a beneficial response to these materials.

The materials studied most for use as synthetic grafts have been calcium phosphate ceramics and bioactive glasses. Calcium phosphate ceramics (CPCs) are very similar in composition to the mineral phase of bone. Bioactive glass are capable of forming a hydroxyapatite layer on their surface that mimics the mineral phase of bone.

The most commonly used calcium phosphate ceramics include: hydroxyapatite (HA), in either dense or porous forms, and β-tricalcium phosphate (β-TCP). Hydroxyapatite is of limited effectiveness as a grafting material. When HA particulate material in porous and dense form was evaluated as a grafting material in the alveolar ridge it was found that fibrous encapsulation formed in perosseous sites. Migration of the particles was also found to be a problem. (Ducheyne P., *J. Biomed. Mater. Res.* (1987) 21(A2 Suppl):219.) Further, HA cannot be used as a scaffolding material since its rate of degradation is slow. (Cornell et al., *Clin. Orthop.* (1992) 297; and Radin et al., *J. Biomed Mater. Res.* (1993) 27:35–45.)

β-TCP, on the other hand, is a biodegradable material which is osteoconductive. However, its degradation rate has been found to be too fast to serve as an effective synthetic graft material in load-bearing situations. (Damien et al., supra.) Thus, clinical evaluations and applications of the HA and β-TCP materials, either dense or porous, have demonstrated that both materials are limited by a lack of controlled rate of reactivity.

Bioactive glasses were first found to bond to living bone by Dr. Larry Hench in the late 1960's. Since that time, more than ten groups around the world have shown that glasses containing $SiO_2$, CaO, $P_2O$, $Na_2O$ and other smaller amounts of oxides in various compositions bond to bone. (Ducheyne P., *J. Biomed Mater. Res.* (1987) 21(A2 Suppl):219; Hench, L. L., *Ann. N.Y. Acad. Sci.* (1988) 523:54; Andersson et al., *J. Biomed Mater. Res.* (1991) 25:1019–1030; Andersson et al., *J. Non-Cryst Solids* (1991) 129:145–151; Boone et al., *J. Biomed Mater. Res.* (1989) 23(A2 Suppl):183; Ducheyne et al., *Clin. Orthop. Rel. Res.* (1992) 76:102–114; Hench, L. L., *J. Biomed Mater. Res.* (1989) 23:685–703; Kokubo, T., *Biomaterials* (1991) 12(2):155; and Rawlings, R. D., *J. Mater. Sci. Letters* (1992) 11:1340–1343.)

Bioactive glass-ceramics undergo surface corrosion reactions when exposed to body fluids. These corrosion reactions form a silica-rich surface layer. This layer serves as a nucleation site for the deposition of calcium phosphate, which evolves into a thick hydroxyapatite layer. When in contact with bone forming cells, this layer will form the basis of the chemical bond between the glass and the bone matrix. (Ducheyne, supra; Hench (1988), supra; and Hench, (1989), supra.) Dr. Hench's 45S5 bioactive glass has been the most extensively studied of the bioactive glass-ceramics. Its composition by weight % is: 45% $SiO_2$, 24.5% CaO, 6% $P_2O_5$ and 24.5% $Na_2O$.

In U.S. Pat. No. 5,204,106 (incorporated herein by reference), 45S5 glass in particulate form in a narrow size range was described as being an effective bone graft substitute in the alveolar ridge model and as being well incorporated into the surrounding bone. The glass granules were described as causing the upregulation of osteoprogenitor cells to osteoblasts that actively lay down bone tissue. (Schepers et al., *J. Oral Rehabil.* (1991) 18:439–452.)

The following parameters are important for bone-bioactive synthetic grafts: controlled resorption and reactivity, immersion induced transformation of the synthetic materials' surface into a biologically-equivalent hydroxyapatite-like mineral, relatively large surface area, and porosity (to create a network for osteoblastic activity). Bioactive glass can potentially be tailored to fit these parameters. In addition, the following requirements are important for a successful delivery system for biologically active molecules: 1) controlled release of the molecules; 2) delivery of adequate amounts of the molecules; 3) rapid growth of bone tissue into the carrier; 4) biocompatibility, osteoconductivity, and osteoinductivity of the implant material; and 5) resorption of the carrier once bone tissue has completely formed. (Lucas et al., *J. Biomed Mater. Res.* (1989) 23(A1 Suppl):23.) No delivery system currently available meets all of these criteria. (Damien et al., supra; and Cornell and Lane, *Clin. Orth. Rel. Res.* (1992) 277:297–311.) Certainly, no delivery system results in controlled delivery.

Attempts have been made to try to improve calcium phosphate ceramics by using them as delivery vehicles for bone growth factors. To date, there has been no success in incorporating growth factors into calcium phosphate ceramics in a way that will lead to a sustained release of the added growth factor. Mostly, one achieves a "burst" release, which is a rapid initial release of most of the material over a short period of time. (Campbell et al., *Trans. Orthop. Res. Soc.,* 40:775, 1994.)

Carriers made of β-TCP, or nonsoluble collagen, have been moderately successful when combined with bone morphogenetic protein in attaining good acceleration of bone tissue healing. (Damen et al., *J. Dental Res.* (1989) 68:1355–1359) However, these systems have not been able to produce a measurable, controlled release of growth factor for time spans approaching those needed for bone tissue regeneration to span large bone filling defects. In one study, large amounts of growth factors, i.e. greater than 50 milligrams, were required to fill defects greater than three (3) centimeters. (Johnson et al., *Clin. Orthop.* (1992) 277:229237.)

In most of the systems studied with osteoconductive materials used as carriers, the method of incorporation has been that of simple immersion of the material into a growth factor solution. The growth factor is then adsorbed either onto the material surface or into the pore structure, but is then quickly released upon immersion in an aqueous solution in a burst effect. (Campbell et al., *Trans. Orthop. Res. Soc.,* 40:775, 1994.)

Published application WO 92/07554 reports a material which can be implanted in living tissue which has a biodegradation rate matching the rate at which the tissue regenerates. It is reported that the material may include an active substance providing an extended therapeutical effect. The material includes a calcium phosphate, biodegradable oxide or polyoxide, and an active substance having amine groupings such as netilmicin and/or gentamicin in sulphate form.

Published application WO 93/05823 reports a composition for stimulating bone growth comprising at least one of FGF, TGF-β, IGF-II, PDGF, and their biologically active mutants and fragments, or bone extracts with corresponding activity, or bone extracts with BMP activity, and a suitable application material.

United Kingdom Patent Application GB 2255907 A reports a delivery system for biologically active growth and morphogenetic factors comprising a solid adsorbent selected for its specific affinity for the factor and the factor adsorbed thereon. In one embodiment, porous hydroxyapatite is specified as the solid adsorbent.

U.S. Pat. No. 4,869,906 describes a resorbable porous tricalcium phosphate in which the pores are sealed with a filler mixture of antibiotic and a filler.

U.S. Pat. Nos. 5,108,436 and 5,207,710 describe stress-bearing prostheses having a porous region in combination with an osteogenic factor extract or a purified osteogenic inductive protein, optionally in combination with a TGF-β cofactor, in a pharmaceutically acceptable carrier. The carrier is either a collagen composition or a ceramic. The osteogenic factor extract is dispersed in the porous region. Other procedures for combining the stress-bearing member with the osteoconductive material including coating, saturation, applying vacuum force to get the material into the pores, and air-drying or freeze-drying the material onto the member. It is further described that the pharmaceutically acceptable carriers preferably include a matrix that is capable of providing a structure for developing bone and cartilage. Some preferred pharmaceutically acceptable carriers listed include collagen, hydroxyapatite, tricalcium phosphate, and bioactive glass. However, there is no description of a preparation containing bioactive glass as a pharmaceutically acceptable carrier.

U.S. Pat. No. 4,772,203 describes implants having a core and a matrix, with the matrix being at least partially resorbable. The resorbable matrix is one or both of bioactive and osteogenesis-inducing. Tricalcium phosphate, hydroxylapatite [sic], and bioactive glass are listed as such matrixes. It is further stated that if a resorbable matrix is employed, it is further possible to embed antibiotics in the latter.

U.S. Pat. No. 4,976,736 describes biomaterials useful for orthopedic and dental applications having a base portion of calcium carbonate and a surface layer of a synthetic phosphate such as hydroxyapatite. One advantage asserted for hydroxyapatite is absorbency. It is further described that antibiotics or growth factors can be introduced into the pore cavities of the implant or attached, respectively. Alternatively, the antibiotic or growth factor can be intermixed with a preferably biodegradable polymer and injected or vacuum infiltrated into the porosity of the phosphate surfaced material.

Gombotz et al., *J. App. Biomat.,* (1994) 5:141–150 describe the incorporation of transforming growth factor-β into a composite implant made from poly(lactic-co-glycolic acid) and demineralized bone matrix. It is reported that the implants exhibited an inflammatory response with little mineralization or bone formation. Similar results were reported in Meikle et al., *Biomaterials*, (1994) 15(7):513–521 with poly DL-lactide-co-glycolide discs having bone matrix extract incorporated therein.

U.S. Pat. No. 4,563,350 describes a composition suitable for inductive bone implants comprising a purified form of osteogenic factor in admixture with a carrier having a percentage of non-fibrillar collagen. The factor is added to the collagen either in solution or gelatin form and stirred in dilute mineral acid for 1–2 hours at approximately 4° C. The material is then dialyzed and lyophilized.

Japanese Laid-Open Patent Publication No. 5253286 describes a bone restoring material comprising Ca-containing glass powder and or crystallized glass powder, an aqueous solution composed mainly of phosphate, and a medical substance in release-controlled form. The medical substance is described as being in particulate form and can be coated with materials capable of oppressing the releasing of the substance temporarily.

As can be seen from the foregoing, a carrier providing for the controlled release of biologically active molecules is needed. Such materials which are additionally osteoconductive and/or osteoinductive are also needed.

Bioactive glasses are osteoconductive but are usually formed by combining the different oxides in a platinum crucible and melting the mixture at a temperature of 1300°–14000° C. This is the melt-derived, or conventional, method of obtaining bioactive glasses. Such temperatures, however, would destroy the function of most biologically active molecules during preparation.

Another method which can be used to synthesize bioactive glass is that of sol-gel processing. Sol-gel synthesis of glasses is achieved by combining a metal alkoxide precursor, such as tetraethylorthosilane (TEOS, $Si(OC_2H_5)_4$ in the case of silica), with water and an acid catalyst to produce a hydrolysis reaction with consequent polymerization of the metal alkoxide species and production of a gel. This gel will consist mostly of the metal oxide when dried and will attain the consistency of glass.

Several investigators have reported the incorporation of proteins into a sol-gel-type glass produced using silicon alkoxide precursors and water with a maintenance of function. Braun et al., *J. of Non-Crystalline Solids*, (1992) 147 and 148:739–743; Yamanaka et al., *Chemistry of Materials*, (1992) 4(3):495–497; Ellerby et al., *Science*, (1992) 255:1113–1115; and Avnir et al., *Encapsulation of Organic Molecules and Enzymes*, Ch. 27, pp385–404, American Chemical Society (1992). Methods for synthesizing low temperature, low alcohol, low proton-concentration sol-gels for enzyme incorporation are described. The incorporated proteins maintained their functionality. However, the focus of such procedures was the immobilization of the protein within the sol-gel in a manner which retains the protein of interest within the gel. When the sol-gel material functions as a sensor, very small molecules, such as glucose, can pass through the pores for assay. The incorporation within the sol-gel provides for repeated use of the protein. Release of the protein from the sol-gel was not desired and would actually be counter to maintenance of long-term activity.

In U.S. Pat. No. 5,074,916, alkali-free bioactive sol-gel compositions based on $SiO_2$, $CaO$, and $P_2O_5$ are described. Compositions ranges are 44–86, 4–46, and 3–15 weight percent, respectively. However, the process described utilizes tempertures around 600°–800° C. Such a process is totally incompatible with the incorporation of biological molecules.

SUMMARY OF THE INVENTION

The present invention is directed to controlled-release carriers. In the carriers according to the invention, biologically active molecules are incorporated within the matrix of a silica-based glass. We have found that a derivation of the sol-gel technique facilitates such incorporation without negatively affecting subsequent activity of the molecules. In the case of pure silica glass, the release of the biological molecules from the carrier is effected primarily by diffusion through the pore structure. In the instance the glass contains oxides in addition to silicon, the release of biological molecules is effected by diffusion and reaction when immersed in fluids such as, for example, body fluids.

The sol-gel derived technique allows extensive control of the glass ultrastructure and, thus, further control over the timing and quantity of release of the biologically active molecules, such as drugs or growth factors. Such carriers can be both osteoconductive and osteoinductive through the formation of a calcium phosphate surface layer (i.e. bioactive) and the release of protein factors that attract and stimulate mesenchymal cells to differentiate into bone forming cells on the carrier surface, as well as increase the proliferation of osteoblasts in the local area. The net effect can be the acceleration of bone tissue regeneration and reduction in the incidence of infection in the area adjacent to the sol-gel/biologically active molecule carrier composite, making the same particularly attractive as implants. The bioactive composite materials have a synergistic effect in promoting bone formation and, as such, can serve as an acceptable substitute for autogenous bone graft material.

In one aspect, the present invention relates to a carrier for controlled release of biologically active molecules over time comprising silica-based glass having biologically active molecules incorporated within the matrix of the glass.

In another aspect, the present invention relates to a method for preparing silica-based glass having biologically active molecules incorporated in the matrix comprising reacting a silicon metal alkoxide with water and methanol in a molar ratio of from about 6:1 to about 20:1 water/alkoxide, adjusting the pH to a value between 1 and 4.5, adding the biologically active molecule, allowing the mixture to gel and age at temperatures from about 0° C. up to about 40° C., and then drying the aged gel at temperatures from about 15° C. to about 40° C.

In another aspect, the present invention relates to a method for preparing silica-based glass having biologically active molecules incorporated in the matrix comprising reacting a silicon metal alkoxide and other alkoxides with water and methanol, adjusting the pH to a value between 1 and 4.5, adding the biologically active molecule, allowing the mixture to gel and age at temperatures from about 0° C. up to about 40° C., and then drying the aged gel at temperatures from about 15° C. to about 40° C.

In another aspect, the present invention relates to a method for preparing pure silica glass having biological molecules incorporated in the matrix comprising reacting a silicon metal alkoxide with water and methanol in a molar ratio of about 10:1 water/alkoxide, a methanol/alkoxide molar ratio of about 1:1, adjusting the pH to a value between 1.5 and 3, adding the biologically active molecule, allowing the mixture to gel and age at temperatures from about 0° C. to about 40° C., and then drying the aged gel at temperatures from about 15° C. to about 40° C.

In another aspect, the present invention relates to a method for delivering biological molecules to a bony defect comprising implanting a material comprising a controlled-release carrier of silica-based glass having biological molecules incorporated within the matrix of the glass in the bony defect.

In another aspect, the present invention relates to method for delivering antibiotics in situ comprising contacting a sample with silica-based glass having antibiotics incorporated within the matrix of the glass.

In another aspect, the present invention relates to a method for preparing a controlled-release carrier comprising silica-based glass having a porous matrix and biologically active molecules incorporated in said matrix comprising combining a silicon alkoxide and calcium alkoxide and mixing under an argon atmosphere for up to about 15 minutes without any water, alcohol, or acid, being added. The biologically active molecules are then added to the mixture in acid and the mixture is allowed to gel and age at temperatures from about 0° C. to about 40° C., and then dried at temperatures from about 15° C. to about 40° C. until a weight loss of from about 50 percent to about 80 percent is achieved.

In another aspect, the present invention relates to a pre-treated carrier comprising silica-based glass having biologically active molecules incorporated within the matrix of the glass. The carrier has been treated by immersion in a solution containing ions typical for interstitial fluid for a period of up to about seven days prior to use.

In another aspect, the present invention relates to an improved implant for filling a bony defect. The improved implant comprises a coating of a silica-based glass having biologically active molecules incorporated within the matrix of the glass.

In another aspect, the present invention relates to a composition for varying release rates of biologically active molecules comprising granules of carriers for controlled release of biologically active molecules over time comprising silica-based glass having biologically active molecules incorporated within the matrix of the glass. To effect the varying release rate, granules of different sizes in the range from about 500 $\mu$mm to about 5 $\mu$m are included.

In another aspect, the present invention relates to a composition comprising different populations of granules of carriers for controlled release of different biologically active molecules over time. The composition comprises silica-based glass having biologically active molecules incorporated within the matrix of the glass, each population having a different biologically active molecule incorporated therein.

DETAILED DESCRIPTION

Figure 1:
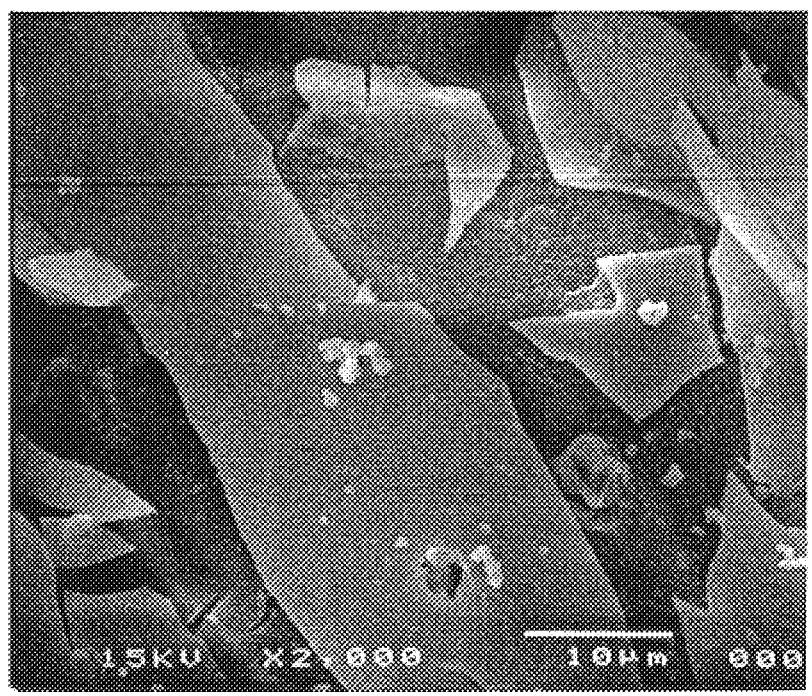
FIG. 1 depicts a scanning electron micrograph of silica-based glass immersed in simulated physiological solution.

Utilizing the method according to the present invention, proteins and other biologically active molecules can be incorporated into silica-based glass carriers in a way that leads to sustained release of the added molecules and does not destroy their function. Such a controlled release delivery system can be used in implant materials, for example, to fill in bony defects, including defects larger than three centimeters without requiring an excessive quantity of growth factors. Such a controlled release delivery system also finds use in other applications with site-specific targeting needs such as, for example, chemotherapy. The carriers can be synthesized under sterile conditions or can be sterilized subsequently using conventional sterilization methods.

Controlled-release carriers according to the invention comprising antibiotics can be used in tissue culture for preventing contamination, particular that which develops upon consumption of antibiotic added with medium, by contacting the carrier with the culture through, for example, immersion.

Controlled release carriers according to the invention comprising growth factors, in particular bone growth factors, can be used to test the effect of the continual, controlled release of different factors on bone cells in vitro. It is also contemplated that such carriers can be used for the development of immortal bone cell lines in vitro.

Sol-gel derived processing can be done at low temperatures—i.e. approximately 40° C. or below—and low pH. Both of these conditions can be important for maintaining the functionality of biologically active molecules incorporated into the sol-gel matrix.

The advantages of sol-gel derived processing include the following: 1) a sol, which is a suspension of colloidal size particles, is in liquid form before it gels; 2) the whole reaction can be done at room temperature; and 3) the microporosity of sol-gel glasses can be controlled by, for example, varying water content, timing of proton addition, proton concentration, aging time, and drying time. The pore sizes achievable with sol-gel processing in general are in the nanometer range. During the liquid phase of the reaction, proteins and other biologically active molecules can be added to the liquid sol before it gels. These molecules then become encased in the solid matrix. Because of the controllable microporosity, a subsequent controlled release of molecule is achieved.

As used herein, "controlled-release carrier" refers to carriers for biologically active molecules, as defined below, which provide for the release of the biologically active molecules over time when immersed in solutions containing, for example, ions typical for interstitial fluid. An example of such a solution is simulated physiologic solution (SPS), used in some of the examples below. SPS is made by dissolving reagent grade NaCl, KCl, $NaHCO_3$, $K_2HPO_4$, $CaCl_2$, $MgCl_2$, and $MgSO_4$ in a 0.05M Tris[hydroxymethly] aminomethane hydrochloride (tris) buffered solution (pH 7.3 at 37° C.) resulting in ionic concentrations similar to plasma: $Na^+$=142 mM, $K^+$5 mM $Ca^{+2}$=2.5 mM, $Mg^{+2}$=1.5 mM, $HCO_3^-$=27 mM, $HPO_4^{-2}$=1 mM, and 0.5 mM $SO_4^{-2}$. Another example is tissue culture medium.

As used herein, "bioactive" refers to a bone bioactive material having a calcium phosphate rich layer present, or which develops during appropriate in vitro or in vivo conditions. As observed by Pereira et al., *J. of Biomed. Mat. Res.*, (1994) 28:693–698 (incorporated herein by reference), pure silica gel having a porous hydrated layer is able to induce a carbonated hydroxyapatite layer when soaked in a simulated body fluid containing calcium and phosphate ions. Pure silica hydrogels produced using TEOS and drying temperatures of around 400° C. were immersed in simulated body fluids having different magnesium, calcium, and phosphate ions. It was reported that apatite nucleation induction periods were decreased with the addition of small amounts of calcium and phosphate ions to the fluids, as well as increase in pH. Li et al., *J. Appl. Biomater.*, (1993) 4:221–229 and Li et al., *J. Amer. Ceram. Soc.*, (1993) 75:2094–2097 (both incorporated herein by reference).

As used herein, "silica-based" refers to the inclusion of a silicon oxide in the composition of the glass. Other oxides may also be present.

As used herein, "biologically active molecules" are defined as those organic molecules having an effect in a biological system, whether such system is in vitro, in vivo, or in situ. Biologically active molecules include, but are not limited to, the following categories: growth factors, preferably bone growth factors, cytokines, antibiotics, anti-inflammatory agents, analgesics, and other drugs. The term "type" as used hereinafter in reference to biologically active molecules refers to biologically active molecules of the previously listed categories, as well as specific compounds, i.e. vancomycin, TGF-β, etc. These specific compounds can be in the same or different categories.

The term "matrix" includes the solid framework of the bioactive glass structure itself, as well as the pores. The phrase "incorporated within said matrix" denotes that the molecules are incorporated throughout the glass network.

The term "bony defect" refers to regions necessitating repair including, but not limited to, fractures, areas of wear and tear, holes resulting from removal of screws and pins, replacements, periodontal applications, and deterioration of bone due to old age or disease.

The term "implant" refers to a material for filling bony defects as described above. The implant preferably comprises a silica-based glass further comprising calcium. The implant can be in the form of granules, discs, blocks, or monoliths, and can comprise the controlled release carrier or simply be coated with the carrier. The implant can also comprise porous materials for use in bone surgery such as porous hydroxyapatite or, as described in WO 94/04657, porous bioactive glass. The term also includes prosthetic devices which, according to the invention, can have a coating, or partial covering, of glass or bioactive glass having biologically active molecules incorporated within the matrix. Examples of such prosthetic devices include, but are not limited to, hip and joint prostheses.

The implant can comprise a "cocktail" providing for a combination of materials and/or release rates. The cocktail can include a population of granules of different sizes, all containing the same type of biologically active molecules. Alternatively, granules containing different types of biologically active molecules can be combined. The granules in such a cocktail can be the same size or different sizes, thereby providing for the release of different molecules at different rates. For example, a cocktail including antibiotics, anti-inflammatory agents, and growth factors can be prepared.

It is also contemplated that two or more types of biologically active molecules can be contained in each implant material as defined herein. This can be effected by simultaneous addition of the molecules into the solution. Alternatively, implants containing one or more biologically active molecules can be prepared and then these implants can, themselves, be coated with, or incorporated within, a solution containing one or more different types of biologically active molecules, and/or at different concentrations.

The term "antibiotic" includes bactericidal, fungicidal, and infection-preventing drugs which are substantially water-soluble such as, for example, gentamicin, vancomycin, penicillin, and cephalosporins.

The term "growth factors" includes growth factors identified as having osteogenic or osteoinductive properties. Included among the many factors identified with the control of bone formation are platelet derived growth factors (PDGF), the transforming growth factors (TGF-β), insulin-like growth factors (IGFs), fibroblast growth factors (FGFs), and the bone morphogenetic proteins (BMPs). These growth factors are present at the site of fracture healing in vivo and are produced at the time of injury through platelet lysis (PDGF and TGF-β) and by the resorption of bone matrix (TGF-β and BMPs). The individual factors will be discussed in more detail below.

The term "contacting" includes, but is not limited to, contacting the carrier with the sample for which release of the biologically active molecules is targeted through, for example, immersion, implantation, and embedding.

The identification of osteogenic and osteoconductive growth factors has spawned the search for new graft substances obtained through genetic engineering concepts. The controlled delivery of these recombinant molecules, however, is important. Growth factors with known effect on bone tissue must be delivered at the site in sufficient doses to stimulate healing. Glasses synthesized following a room temperature sol-gel-derived procedure are outstanding candidate materials for the controlled release of such osteoinductive molecules. The processing of the glass allows one to control the ultrastructure of the glass such that the timing and quantity of release are tailored to fit the specific therapeutic needs. In addition, these glasses can be osteoconductive, thereby providing a substrate for bone tissue development.

The effects of the growth factors when exogenously applied to in vitro and in vivo experimental models of bone formation have demonstrated their biological properties. (Cornell et al., supra; and Mohan et al., supra.)

Consequently, any material which affords the sustained delivery of such factors is beneficial. Although most of the previous studies clearly demonstrate the osteogenic and osteoinductive effects of these proteins, the precise biological properties of these growth factors with respect to the degree of bone formation is greatly influenced by the following: the environmental conditions of the experimental model, the timing, method and dose of growth factor delivery, the hormonal milieau and the synergy between the various growth factors. Thus, the present invention provides a method to elucidate the effects of these growth factors.

From a developmental point of view, the formation of bone occurs in a series of discrete steps. Initially there is a proliferative phase followed by cellular differentiation and deposition of a collagenous matrix which in itself influences subsequent expression of bone proteins. (NIH/AAOS sponsored workshop, supra.) Some workers view collagenous matrix synthesis as a series of temporal events in which there is an initial collagenous phase followed by a rise in alkaline phosphatase activity and the expression of osteonectin, bone sialoprotein and osteocalcin. Osteopontin expression and synthesis has been further dissected temporally in terms of sulfation, phosphorylation and molecular size. Aside from the proteins listed above, other studies have shown that at least two forms of chondroitin sulfate proteoglycan are also synthesized by the osteoblast. These parameters can all be measured by methods well known in the art. Some growth factors are detailed below.

Insulin-like growth factor (IGF) I and II are made by bone cells as well as by other tissues throughout the body. They are found in bone matrix and have presumably been secreted by bone cells. (Canalis et al., *Calcified Tissue Int.* (1993) 53:S90–S93; and Canalis et al., *J. Bone Miner. Res.* (1993) 8:S237.) In vitro, IGFs have been shown to increase bone collagen and matrix synthesis, to increase osteoblast-precursor replication and decrease bone collagen degradation. (Hock et al., *Endocrinology* (1988) 122(1):254; and Mccarthy et al., *Endocrinology* (1989) 124(1):301.)

Growth hormone is thought to act through IGF in stimulating bone growth, but it has also been shown to have local effects on mesenchymal cell proliferation and differentiation. (Downes et al., *J. Mater. Sci.:Mater. Med.*, (1991) 2:176–180; and Silbermann, M., *Biomaterials*, (1990) 11:47–49.) Human growth hormone has two molecular weight species, one of 20,000 and the dominant species of 22,000.

Platelet derived growth factor (PDGF), a polypeptide of approximately 30 kD in molecular weight, exists as a dimer composed of two A subunits or two B subunits or as a heterodimer of an A and a B subunit, creating three separate forms of PDGF. These subunits are the products of two separate genes. While all three forms are found in bone matrix, only PDGF AA is made and secreted by bone cells in vitro. PDGF BB has been found to be the most active of the three forms. (Mohan et al, supra.)

PDGF has been shown to have bone resorbing activity in vitro; a number of investigators have reported increased bone resorption in response to administration of physiological doses of PDGF. (Tashjian et al., *Endrocrinology* (1982) 111:118–124.) Additionally, PDGF has been shown to increase osteoprogenitor cell replication.

Transforming growth factor-beta (TGF-β) is a family of molecules which may have bone promoting properties for fractures. TGF-β is a homodimeric peptide with a molecular weight of 25 kD. The most abundant sources of this molecule are platelets and bone. This multifunctional peptide has a broad range of cellular activities, including control of the proliferation and expression of the differentiated phenotype of several cell types specific to bone, among them mesenchymal precursor cells, chondrocytes, osteoblasts, and osteoclasts. (Beck et al., *J Bone Miner. Res.* (1991) 6(9):961; Joyce et al., *Orthop Clin. North Am.* (1990) 21(1):199; and Joyce et al., *J. Cell Biol.* (1990) 110(6):2195.) Although it exists in several distinct forms, two of these, TGF-β1 and 2, have been isolated from bone in approximately a 4:1 ratio. In vivo studies based on both immunohistochemical staining and in situ hybridization have demonstrated the synthesis of TGF-β by both chondrocytes and osteoblasts and the accumulation of TGF-β in models of endochondral ossification. (Joyce et al., *Orthop Clin. North Am.* (1990) 21(1):199; and Joyce et al., *J. Cell Biol.* (1990) 110(6):2195.) In a study in which TGF-β 1 or 2 was introduced by daily injection into the subperiosteal region of newborn rat femurs, (Joyce et al., *J. Cell Biol.* (1990) 110(6):2195) demonstrated that mesenchymal precursor cells in the periosteum were stimulated by TGF-β to proliferate and differentiate in much the same manner as that which is observed in embryological bone formation and early fracture healing. After the cessation of injections, endochondral ossification also occurred, resulting in the replacement of cartilage with bone.

The implantation of a bone morphogenetic protein (BMP) solution leads to a series of developmental processes including chemotaxis, proliferation, and differentiation, which result in the transient formation of cartilage and its replacement by living bone tissue complete with hematopoietic marrow. (Urist, M. R., *Science* (1965) 150:893–899.) Several newly discovered factors, BMP-1 through 7, and osteoinductive factor (OIF) have been implicated in the BMP process. BMP-2 through 7 are all members of the TGF-β superfamily of molecules and are closely related to two factors Vg1 and DPP which are involved in a variety of developmental processes during embryogenesis. Both BMP-2A and BMP-7 have been expressed as recombinant proteins both of which have been shown to clearly induce the entire cartilage and bone formation process seen with bone-derived BMP solutions. (Wozney, J. M., *Prog. Growth Factor Res.* (1989) 1(4):267.) At the present time, two BMPS: BMP-2A (Gerhart et al., *Clin. Orthop.* (1993) 317; Wozney et al., *Science* (1988) 242(4885):1528; and Yasko et al., *J. Bone Joint Surg.* <Am> (Aug. 1992) 74(7):1111 and *J. Bone Joint. Surg.* <Am> (1992) 74(5):659) and BMP-7 (Sampath et al., J. Biol. Chem. (1992) 267(28):20352) (also known as OP-1) have been demonstrated to increase bone formation at extraosseous sites, and to enhance fracture healing. (Gerhart et al., *Clin. Orthop.* (1993) 317.) Purified BMP has been utilized in femoral and tibial non-unions in uncontrolled clinical trials. (Johnson et al., *Clin. Orthop.* (1988) 230:257–265; Johnson et al., *Clin. Orthop.* (1988) 236:249–257; and Johnson et al., *Clin. Orthop.* (1990) 234.)

Current state of knowledge suggests that the local growth factors most likely to increase fracture healing significantly are PDGF, TGF-β and BMP-2.

Maintenance of function of growth factors after incorporation within the silica-based glasses can be tested using the aforementioned techniques for determining bone differentiation. The maintenance of function of antibiotics can be ascertained using standard disc susceptibility tests such as are described in *Antibiotics in Laboratory Medicine*, 3rd edition, V. Lorian, ed., chapter 2, Williams and Wilkins, Baltimore, Md., 1991 (incorporated herein by reference). Function of incorporated anti-inflammatory agents and analgesics can be ascertained by, for example, testing for inhibition of prostaglandin synthesis in cell culture.

Sol-gel-derived glass synthesis

Pure silica and calcium containing glasses have been synthesized with biologically active molecules incorporated therein. Briefly, a silicon alkoxide precursor, preferably tetramethylorthosilane (TMOS), in pure solution is combined with deionized water and stirred by magnetic or ultrasonic means. The water to TMOS molar ratio affects porosity and specific surface area of the gels, which, in turn, affect bioactivity. As both increase, so can bioactivity. To increase both, water is provided in amounts exceeding stoichiometric, or in an $H_2O$/TMOS molar ratio ranging from about 6:1 to about 20:1. In a preferred embodiment the molar ratio of $H_2O$/TMOS is 10:1. Alcohol, preferably methanol, can be added at an alcohol/TMOS molar ratio of from about 0:1 to about 1:1. Acetic acid (0.1N) or HCl (0.1N) can be used as a catalyst for the hydrolysis reaction, and is added to maintain the desired pH, as disclosed below.

Calcium methoxyethoxide (20% solution in methoxyethanol, Gelest Inc., Tullytown, Pa.) can be used as a calcium alkoxide source. Calcium methoxyethoxide (CME) is added in an amount sufficient to result in a final percentage of up to about 40% by weight calcium oxide upon drying of the gel. Triethyl phosphate can be used as a phosphorous pentoxide source. Triethyl phosphate (TEP) can be added to achieve a final concentration of phosphorous pentoxide, $P_2O_5$, up to about 10% by weight upon drying. Weight percentages throughout are calculated based upon the reactions going to completion and complete drying. The water, TMOS, and acid are mixed using sonication in an ice bath, or magnetic stirring, or a combination of both. When a calcium alkoxide is present, the TMOS, calcium alkoxide and additional alkoxides, if any, are preferably mixed under non-aqueous conditions under an argon atmosphere using either magnetic stirring or sonication for up to about one hour.

Since the biologically active molecules to be incorporated retain their biological activities after treatment in moderate to highly acidic conditions, an amount of acid necessary to maintain acidity in a range of pH from about 1–4.5, preferably about 1.5–3, prior to, or during, incorporation of biologically active molecules is used.

The biologically active molecules to be incorporated are added at concentrations resulting in final concentrations ranging from about 0.0001 to about 10% by weight of the glass.

Glasses with compositions of silicon in the range of 60–100% (by weight) with the remainder as other oxides can be prepared. The liquid sol can be cast into a polystyrene container. The sol is aged and allowed to gel in a sealed container. Aging can take from about one (1) day to about four (4) weeks. Drying can be performed for a time of from about 1 to about 14 days.

In order for sol-gel derived glass to be an effective carrier for biologically active molecules, the process should be carried out at a low temperature (about 2°–40° C.) and, in the case of pure silica glass, the acidity of the sol should be between pH 1 and 4.5. Temperature, sol pH, % calcium content, water to TMOS molar ratio and other factors affect the gelling time of the sol. However, when incorporating biologically active molecules, the gelling time of the sol should allow enough time in the liquid state to enable the addition of the biologically active molecule solution for incorporation, cast, and homogeneously mix the sol. Gelation occurs when enough cross-links have formed such that the network spans the length of the container. Gross observation reveals little or no movement of the cast material upon inversion.

A lower pH increases the gelling time. A higher calcium content decreases gelling time. A higher gelling time is desirable in order to see more of the sol-gel reactions going to completion, thus ending with a final material with less porosity and smaller pore size. Less porosity also means a more mechanically strong material with longer times of protein release. However, there are instances when greater porosity may be desirable, for example, achieving a more rapid release of molecules, or a more rapid degradation of the carrier. Larger pore sizes facilitate the release of larger molecules through diffusion.

A lower temperature also increases gelling times. To achieve lower temperatures, the reaction is then carried out in an ice-cooled water bath. A higher water content will also decrease gelling time for most metal alkoxides, although the porosity may stay high due to increased water evaporation from the material. Conditions are selected such that gelation optimally occurs within a period ranging from at least about 30 minutes to about 48 hours for incorporating biologically active molecules. Gelation can be performed at temperatures ranging from about 0° C. to about 40° C.

Aging of the sol-gel occurs after casting and is performed by keeping the casting container sealed. Sol-gel reactions continue unimpeded during this period. Aging can be performed at temperatures ranging from 0° C. to about 40° C. Longer aging times (of up to 1 month) result in a more mechanically strong material, which undergoes less cracking than materials that have been aged for lesser time periods. Aging at a lower temperature, such as 4° C., also extends the gelling time.

Drying temperature and time can also affect the final material characteristics. A fast rate of drying can produce cracks in the final material. The final material loses about 50–80% of its weight between casting and final drying due to evaporation of water, and alcohols produced as by-products of the reaction. Drying is performed at temperatures ranging from about 15° C. to about 40° C. by unsealing the casting container, and can be performed at atmospheric pressure, or pressures lower than atmospheric.

As is evident from FIGS. 3, 7, 8, and 4, the release kinetics of the biologically active molecules in the early stages of immersion, i.e. from about one day to seven days, is higher than those in the later stages. At about seven days after immersion, a major change in the slope of the curves is observed, representing a major change in rate of release. The early higher release is not a "burst" effect as previously reported by several authors (cited above). This higher early release is advantageous when a dual treatment regimen is imposed—an acute treatment at a high dose, followed by a "chronic" lower dose. In cases when a steady state release is desired right from the onset of the medical treatment, i.e., a release without major changes in rate, the sol-gel carriers can be treated by immersion at the time of production such that the intitial higher release phase has taken place before actual use in the patient.

EXAMPLE 1

Synthesis of Sol-gel/Vancomycin Composite

A sol-gel derived silica-based matrix-vancomycin composite was synthesized employing a room-temperature, low acidity, low alcohol concentration procedure. Vancomycin was selected as the drug to be released due to its proven efficacy against gram positive cocci, especially staphylococci, which is a major cause of osteomyelitis. Vancomycin is a water soluble (up to 100 mg/ml) tricyclic glyceropeptide of approximately 3,300 molecular weight.

The material was prepared as follows: 19.6 ml tetramethylorthosilicate (TMOS, Aldrich, St. Louis, Mo., U.S.A.), 14.2 ml water, 5.2 methanol and 0.01 ml of 1N HCl was sonicated in a glass beaker in an ice bath for 30 minutes. Then, 4 ml of the sol was cast into 23 mm diameter polystyrene vials (Sarstedt, Princeton, N.J.) and 1 ml of 10 mg/ml vancomycin HCL (Lederle, Carolina, Puerto Rico) was added to the sols in the vials and the samples were mixed. The same amount of water, i.e. 1 ml, was added to control samples. The total $H_2O$/TMOS ratio was 10:1. The methanol/TMOS ratio was 1:1. The amount of incorporated vancomycin to sample weight was about 1%. The vials were sealed with airtight caps, gelled, aged, and dried at room temperature. Time to gelation varied from 15 to 25 hours. Addition of the vancomycin solutions did not change significantly the time to gelation.

After aging for 2 weeks in the sealed containers, the sols were exposed to air for drying. During drying, evaporation of liquid from the gel pore network resulted in weight loss and shrinking of the gels. The weight loss continued up to 2 weeks. Drying was considered to be complete when the weight loss reached 75–78%. The significant weight loss and shrinking did not produce visible cracks. The resulting products were transparent monoliths in a shape of 11 mm diameter and 8 mm high cylinders weighing 1.1 gram. The density of the dried gel material was equal to 1.5 g/cm$^3$. Since 10 mg vancomycin was incorporated into each of the discs, the vancomycin content in the material was 0.91%. There is no reason to expect that other water-soluble antibiotics will behave any differently.

EXAMPLE 2

Vancomycin Release Study

For the in vitro vancomycin elution study, a part of the monoliths was crushed, ground, and sieved to obtain either small granules in a size range from about 500–700 μm, or large granules of about 5×5×2 mm. The rest of the monoliths were tested as discs.

The synthesized vancomycin composite was immersed into a simulated physiological solution (SPS) with ion content similar to that of plasma as disclosed previously. To determine the effect of the sample surface area to volume (SA/V) ratio, the material used for the immersion experiments was shaped as follows: small granules of 500–700 μm (SA/V approximately 10 mm), large granules 5×5×2 (SA/V=1.5 mm$^{-1}$), discs 11 mm diameter×4 mm (SA/V=0.85 mm$^{-1}$), and half-cylinders 5.5 mm×4 mm (SA/V=1.2 mm−1).

All the samples were immersed at the same vancomycin content in sample/solution ratios equal to 1 mg vancomycin per 1 ml. The immersed samples were incubated at 37° C. for time periods ranging from about 1 hour to about 3 weeks. The solutions were totally exchanged at the following time periods: 1 hour and 1, 3, 7, 14, and 21 days.

Figure 3:
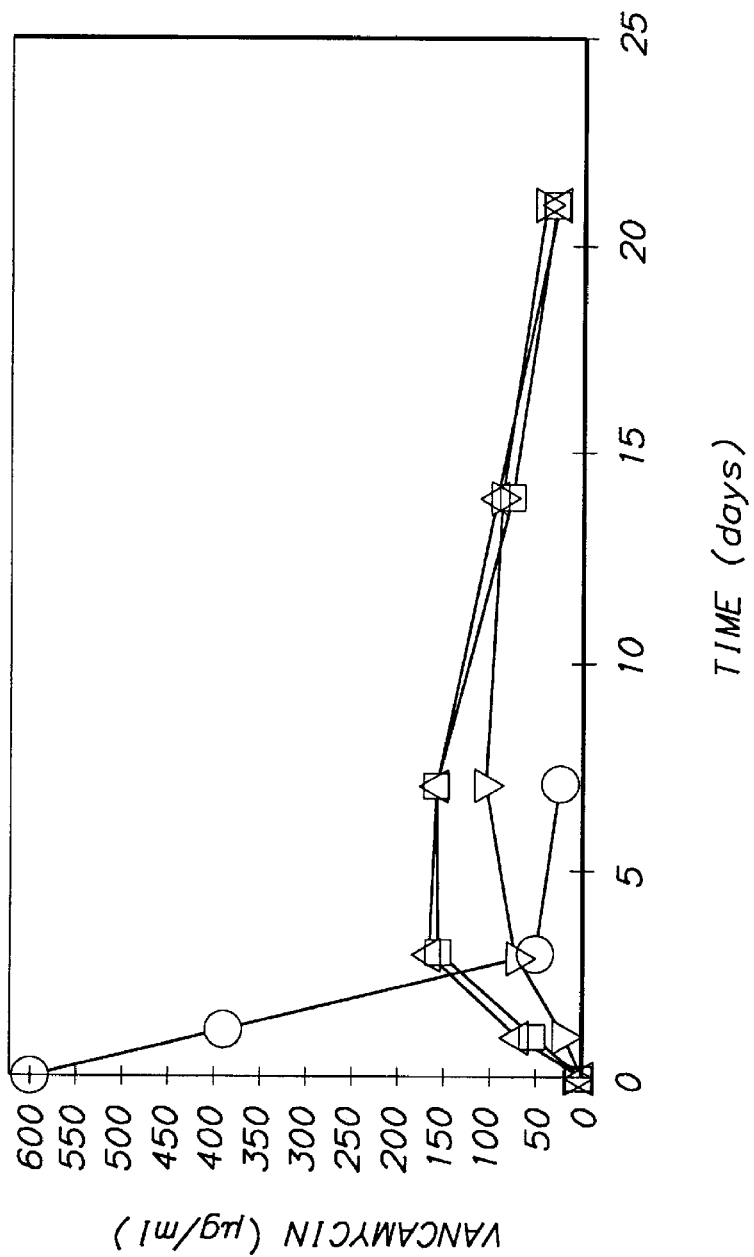
FIG. 3 depicts the release of vancomycin, over time, from granules and discs of pure silica glass immersed in a simulated physiological solution.

The released vancomycin concentrations were measured using an automated Fluorescent Polarizing Immunoassay system (TDxR system, Abbott Diagnostics, Irving Tex.). The results of the vancomycin release assay are presented in FIG. 3 and summarized in Table I below. In FIG. 3, open circles represent the small granules. Open triangles represent the large granules. Open squares represent the 11 mm diameter discs. Open inverted triangles represent the 5.5 mm diameter discs.

TABLE I

| Sample | Release Time (days) | %, Released/Incorporated Vancomycin |
|---|---|---|
| Small Granules | 6 | 100 |
| Large Granules | 21 | 55 |
| Disc (SA/V = 1.2 mm$^{-1}$) | 21 | 48 |

As indicated by the foregoing data, the vancomycin release rate was affected by the material shape, i.e. the material surface area to volume ratio. Specifically, the vancomycin release from the small granules was very rapid and most of the incorporated vancomycin was released during the first day of immersion. In contrast, the large granules (SA/V=1.5 mm$^{-1}$) and discs (SA/V=1.1 or 0.8 mm$^{-1}$) showed a continuous vancomycin release, which started at one hour, gradually increased to a maximum, then slowly decreased, tailing-off up to 3 weeks later. The maximum vancomycin release was measured during the period of immersion between three days and one week.

These findings indicate that the SA/V ratio can affect the release of materials. Combination of the materials of varying shape, i.e. varying SA/V ratio, can provide a controlled vancomycin release which starts upon immersion and continues for up to one month.

EXAMPLE 3

Effect of Vancomycin Concentration

The sol-gel derived silica based matrix-vancomycin composites with varying vancomycin content were synthesized. The sols were prepared as disclosed above in Example 1. Then, 1.2 ml of the sol were cast into 23 mm diameter polystyrene vials. The cast sols were divided into two groups and 0.3 ml of solutions with different vancomycin concentrations were added to the cast sols of both groups in order to keep the same $H_2O$/TMOS molar ratio of 10:1. The amounts of the incorporated vancomycin were 10 and 20 mg for groups 1 and 2, respectively. The percentage of vancomycin to sample weight was equal to 2.8 and 5.5%, respectively. The sols were gelled, aged, and dried to about 75% weight loss.

Ultrastructure parameters of the sols such as specific surface area (SSA), average pore size (PS), and pore volume (PV) of the dried sols were determined using the monolayer gas absorption technique (multipoint B.E.T., Quantachrome). The measured values were as follows:

| | |
|---|---|
| SSA, m$^2$/g | 545 |
| PS, nm | 1.8 |
| PV, cc/g | 0.45 |

Figure 4:
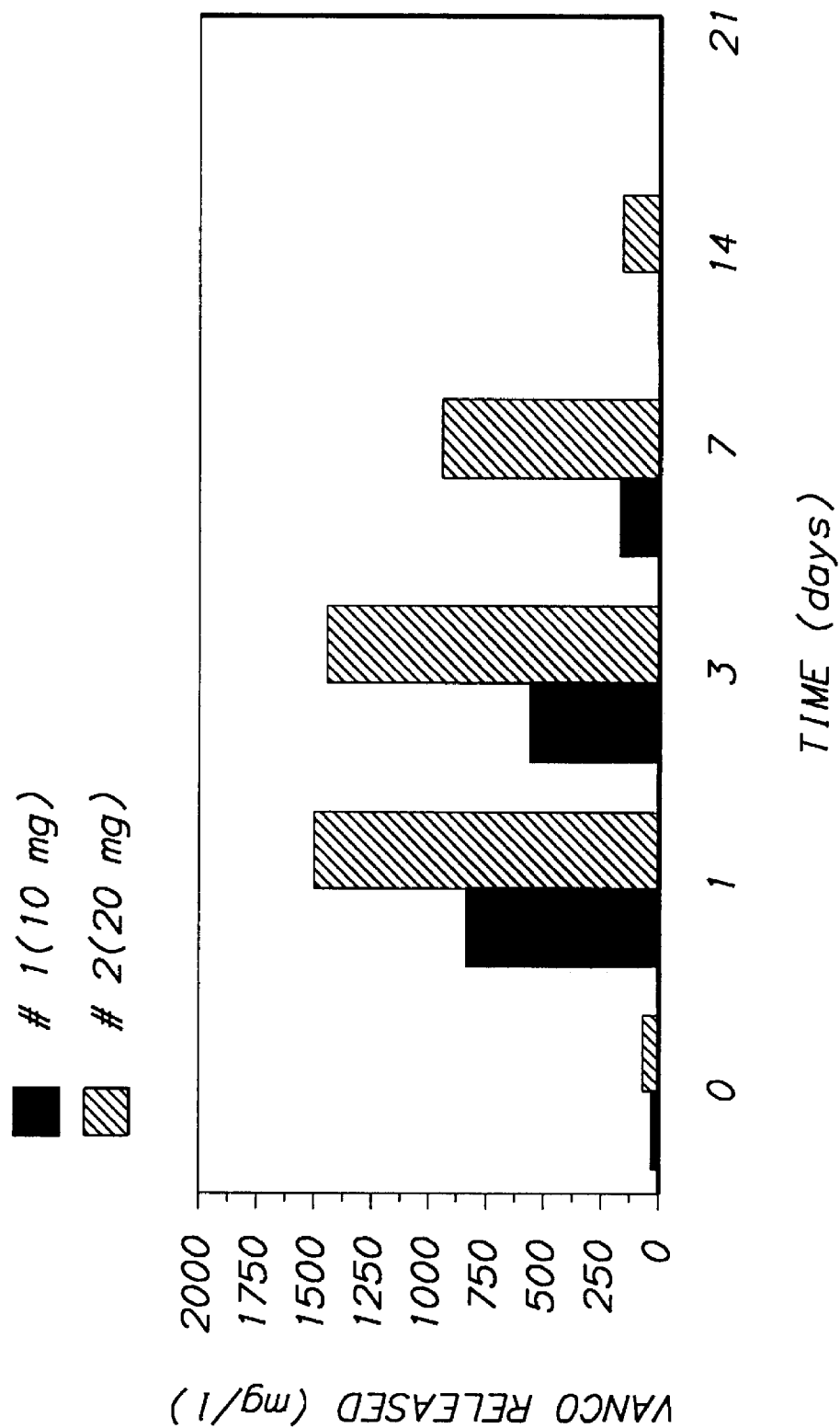
FIG. 4 depicts the effect of concentration on vancomycin release versus time.

The obtained sol-gel derived discs, 11 mm diameter×2 mm, with SA/V ratio equal to 1 mm$^{-1}$, were subjected to vancomycin release study as disclosed above in Example 2. The discs were immersed into 5 ml SPS. The vancomycin content in sample (total weight of vancomycin) to solution volume ratios (Wv/V) were 2 and 4 for groups 1 and 2, respectively. The concentrations of released vancomycin were measured as described above in Example 2. The results of the study are presented in FIG. 4. In FIG. 4, solid bars represent vancomycin at 10 mg incorporation. Hatched bars represent vancomycin at 20 mg incorporation.

The data show that the amount of released vancomycin increased with the amount of incorporated drug. Thus, the released amount appears to be a function of the incorporated quantity (at conditions otherwise equal). However, the drug release profile over time appears to be similar for different concentration. Specifically, the drug release started right after immersion, reached a maximum by 3 days, then gradually decreased.

EXAMPLE 4

In vitro Bacteria Inhibition Test

The SPS solutions with varying contents of vancomycin, released from the sol-gel derived silica-based matrix from the experiments described in Examples 2 and 3, were tested for susceptibility of *Staphylococcus aureus* bacteria to the released drug. The standard disc susceptibility test technique was applied (See Lorian, supra.). The sample SPS solutions with vancomycin released during immersion were tested and compared with standard solutions of vancomycin in SPS with concentrations ranging from 100 to 10,000 $\mu$g/ml. Concentrations of the sample SPS solutions with vancomycin released during immersion were measured using the Fluorescent Polarizing Immunoassay described previously. Single, twenty $\mu$l aliquots of each solution (either standard or sample) were deposited onto ½ inch filter paper discs (#740-E, Schleicher & Schnell, Keene, N.H.). The drug solution impregnated discs were then dried and stored in a desiccator at 4° C. A blood agar plate inoculated with *Staphylococcus aureus* (ATCC 25923) was obtained from the Microbiology Laboratory, Hospital of the University of Pennsylvania. A $1.5 \times 10^8$ CFU/ml suspension of bacteria in 0.45% saline was created to match a McFarland Equivalence Turbidity Standard 0.5 (Remel, Lienexa, Kans.). Mueller-Hinton agar plates, 15×100 mm (Model 01-620, Remel, Lienexa, Kans.) were inoculated with 10 $\mu$l of the *Staphylococcus aureus* suspension by streaking with a sterile swab soaked in the suspension over the entire agar surface to ensure an even distribution of inoculum (standard inoculation procedure). A vancomycin impregnated disc was placed in the center of each agar plate. The agar plates were then incubated in a humidified air environment in a single-chamber, water-jacked incubator (Model 3159, Forma Scientific, Marrietta, Ohio) at 37° C., for 24 hours. Zones of bacteria inhibition were measured using a caliper with a precision of 0.1 mm. The data are presented in FIGS. 5 and 6.

Figure 5:
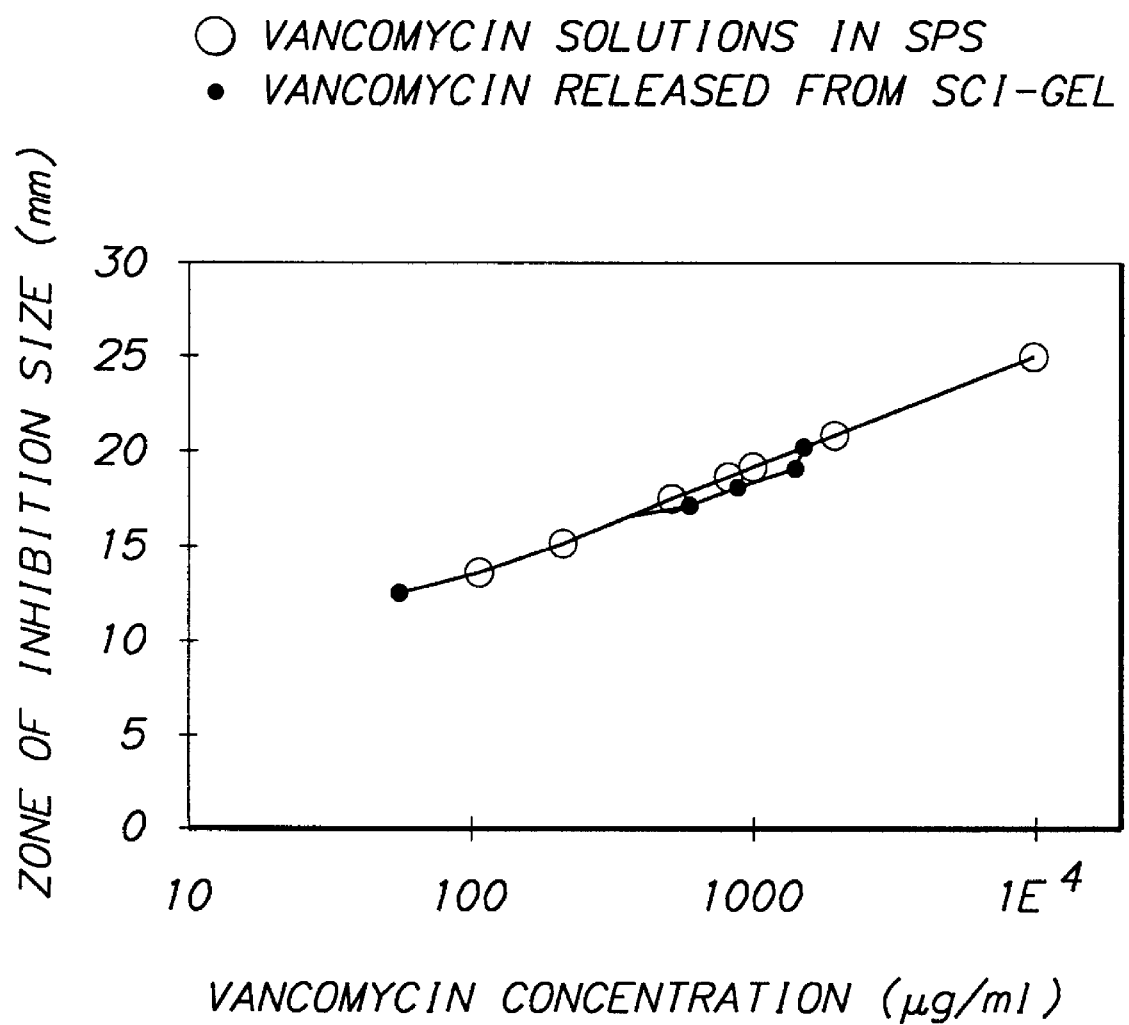
FIG. 5 depicts a comparison of the zones of bacteria inhibition of vancomycin dissolved in simulated physiological solution and vancomycin released from pure silica glass.

The measured zone of inhibition sizes plotted against vancomycin concentration in a logarithmic scale of vancomycin released from sol-gel, as disclosed in Example 3, are presented in FIG. 5. In FIG. 5, open circles represent vancomycin dissolved in SPS. Closed circles represent vancomycin released from the sol-gel carrier.

The discs, impregnated with 30 $\mu$g of vancomycin, either dissolved in SPS or released from the silica-based matrix, exhibited a zone size greater than 12 mm. According to the Zone Diameter Interpretive Standards (Lorian, supra, Tab. 2.1.), a zone of that size indicates that bacteria are susceptible to the material, and the equivalent minimum inhibitory concentration breakpoint is less than 4 $\mu$g/ml. The concentration-zone of inhibition relationship for the sample solutions of vancomycin released from the silica-based matrix showed a close fit to that of the standard solutions.

Figure 6:
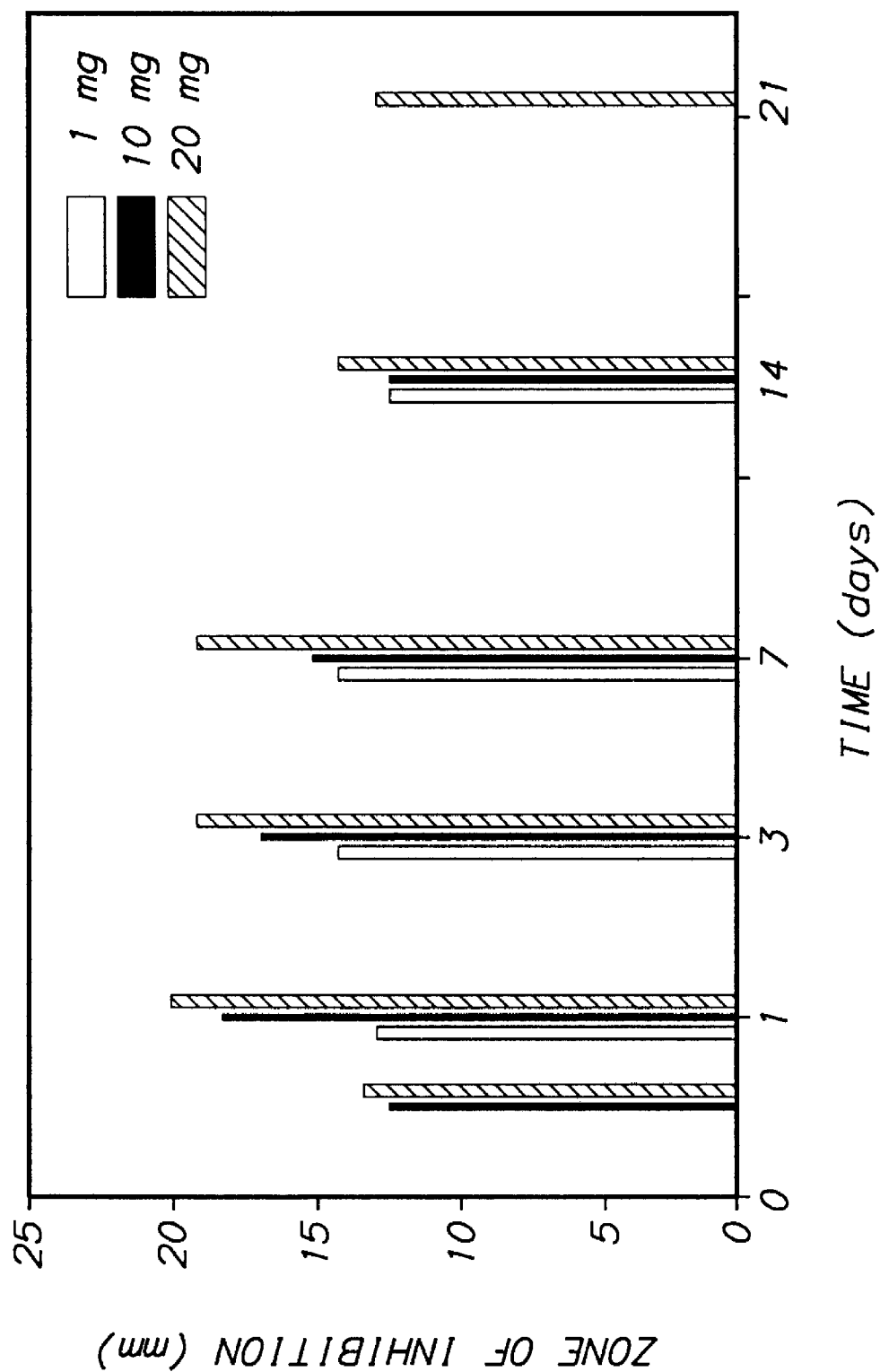
FIG. 6 depicts the zone of bacteria inhibition size versus immersion time and concentration of vancomycin released from pure silica glass.

FIG. 6 shows zone of bacteria inhibition sizes versus immersion time and concentration of vancomycin incorporated into the sol-gel derived silica matrix. Open bars represent vancomycin at 1 mg. Solid bars represent vancomycin at 10 mg. Cross-hatched bars represent vancomycin at 20 mg. The data demonstrate that vancomycin released from the sol-gel matrix was effective to inhibit the bacteria growth up to three (3) weeks (at 20 mg concentration). The measured zone of inhibition sizes appear to increase with concentration of incorporated vancomycin, reflecting larger quantities of released vancomycin.

The foregoing experiments demonstrated the following: incorporation of vancomycin into the silica-based matrix using the sol-gel technology provides a controlled drug release over time, starting upon immersion (and thus implantation) and continuing for at least 3 weeks; and the employed room temperature, low acidity, low alcohol concentration sol-gel procedure did not alter the vancomycin properties since vancomycin released from the sol-gel derived material is as effective in inhibiting bacteria as vancomycin solutions that were not obtained from a sol-gel carrier.

EXAMPLE 5

Synthesis of Sol-Gel/Trypsin Inhibitor Composite

Sol-gel derived glass discs with trypsin-inhibitor incorporated inside their matrix have been successfully synthesized. Trypsin Inhibitor (SIGMA) is a protein with molecular weight of 21 kD. The sol-gel/protein composite contains 1–10 mg Trypsin Inhibitor (TI) per 150–200 mg disc. Protein elution was measurable in samples with 2 mg or greater of protein per disc.

The procedure used to synthesize 1 gram (by dry weight) of the sol-gel derived glass was as follows: 2.48 ml of TMOS (Aldrich, St. Louis, Mo.) was combined with 2 ml DI water and 0.68 ml of methanol in a 30 ml beaker and mixed for 5 minutes using magnetic stirring. This resulted in an $H_2O$/TMOS molar ratio of 10:1 and a methanol/TMOS molar ratio of 1:1. Then, 0.01 ml of 1N HCl was added to catalyze the sol-gel reaction. This results in a clear one phase solution which is stirred for 15 minutes. The sol was cast in 0.8 ml volumes into polystyrene containers and the trypsin inhibitor solution was added in a volume of 0.2 ml of 0.1N acetic acid solution with protein concentration in the range of 1–10 mg/ml. The solution was mixed with vortexing and the containers were capped. Gelling occurred within 1–4 days after casting. The capped sol was allowed to gel and age for times ranging between 1 day to 2 weeks depending on the desired porosity at room temperature. After aging, the sol-gel was allowed to dry at either room temperature or 37° C. by uncapping the casting container. Any liquid produced was decanted off the solid. A higher drying temperature increased the porosity and rate of shrinkage. After drying, the resulting solid had lost 60–70% of its original weight due to evaporation of water and alcohol (methanol is a by-product of the sol-gel reactions).

The resulting solid material was a porous three-dimensional network/polymer of silica which releases incorporated biomolecules in a controlled release fashion. The various processing parameters are depicted in Table II. Sample designations are of the Formula SxxxCxxPxx (date cast), where "Sxxx" is the calculated % silica, "Cxx" is the calculated % calcium oxide, and "Pxx" is the calculated % phosphorous pentoxide. The date cast is presented as the "last two digits of the year.month.day." The trypsin inhibitor content and form of the sample is indicated in the basic Formula TI=X-[sample shape] where "X" is the amount of trypsin inhibitor in mg per sample. The effect of pH on gelling time is apparent from Table II.

TABLE II

| Processing Parameters | Units | | | | | |
|---|---|---|---|---|---|---|
| Sample (Laboratory Designation) | | S100 (94.4.18) | S100 (94.4.18) | S100 (94.4.18) | S100 (94.4.18) | S100 (94.4.18) |
| TI = amount of trypsin inhibitor in mg | | TI = 2– [granules] | TI = 3– [granules] | TI = 5– [granules] | TI = 7.5– [granules] | TI = 10– [granules] |
| Water/TMOS Ratio | | 10 | 10 | 10 | 10 | 10 |
| Methanol/TMOS Ratio | | 1 | 1 | 1 | 1 | 1 |
| Acid Catalyst (amount and concentration) | ml and N | 0.1 ml 1 N HCl | 0.1 ml 1 N HCl | 0.1 ml 1 N HCl | 0.1 ml 1 N HCl | 0.1 ml 1 N HCl |
| % Silica calculated | | 100 | 100 | 100 | 100 | 100 |
| % Calcium Oxide calculated | | 0 | 0 | 0 | 0 | 0 |
| % Phosphorous Pentoxide calculated | | 0 | 0 | 0 | 0 | 0 |
| pH as cast | | 2.3 | 2.4 | 2.8 | 3 | 3.2 |
| Gelling Time | hours | 168 | 144 | 120 | 72 | 24 |
| Volume cast | ml | 1 | 1 | 1 | 1 | 1 |
| Weight as cast | mg | 1003.3 | 1009.2 | 1007 | 997.2 | 960.9 |
| Total Protein in sample | mg | 2 | 3 | 5 | 7.5 | 10 |
| Aging Time | days | 7 | 7 | 7 | 7 | 7 |
| Drying Time | days | 5 | 5 | 5 | 5 | 5 |
| Drying Temperature (degrees centigrade) | C | 20 | 20 | 20 | 20 | 20 |
| Weight after drying | mg | 384.8 | 390.2 | 382.5 | 391.4 | 363 |
| % Weight loss | % | 61.6 | 61.3 | 62 | 60.8 | 62.1 |

EXAMPLE 6

Trypsin Inhibitor Release

The initial release kinetic studies were carried out by immersing the sol-gel/protein composite (100 mg sol-gel/1 mg protein for each sample) in deionized water inside containers which were siliconized in order to reduce protein binding. The protein content in water was measured at different time points. The water was replaced fresh after each time period. The collected fluid that had been in contact with the sol-gel/protein composite was analyzed for protein content using a colloidal gold/spectrophotometric method (Integrated Separation Systems, Natick, Mass., Stoscheck et al., Anal. Biochem., (1987) 160:301–305, incorporated herein by reference) with sensitivity down to 0.5 $\mu$g/ml. The results are depicted in Table III below.

The numbers in the table represent protein release in $\mu$g of trypsin inhibitor after immersion in DI water. Results for each time point are provided together with cumulative protein release.

TABLE III

| | Protein Released $\mu$g | | | | |
|---|---|---|---|---|---|
| Immersion Time: | 3 days | 1 week | 2 weeks | 3 weeks | 4 weeks |
| Sample Designation* | | | | | |
| S100(94.4.18)TI2 | | 75 | 38 | 20 | 16 |
| cumulative release: | | 75 | 113 | 133 | 149 |
| S100(94.4.18)TI3 | | 115 | 56 | 33 | 27 |
| cumulative release: | | 115 | 171 | 204 | 231 |
| S100(94.4.18)TI5 | 75 | 82 | 48 | 30 | 33 |
| cumulative release: | 75 | 157 | 205 | 235 | 268 |
| S100(94.4.18)TI7.5 | 142 | 97 | 70 | 68 | 78 |
| cumulative release: | 142 | 239 | 309 | 377 | 455 |
| S100(94.4.18)TI10 | 175 | 125 | 80 | 55 | 67 |
| cumulative release: | 175 | 300 | 380 | 435 | 502 |

*For key see Table I.

Figure 7A:
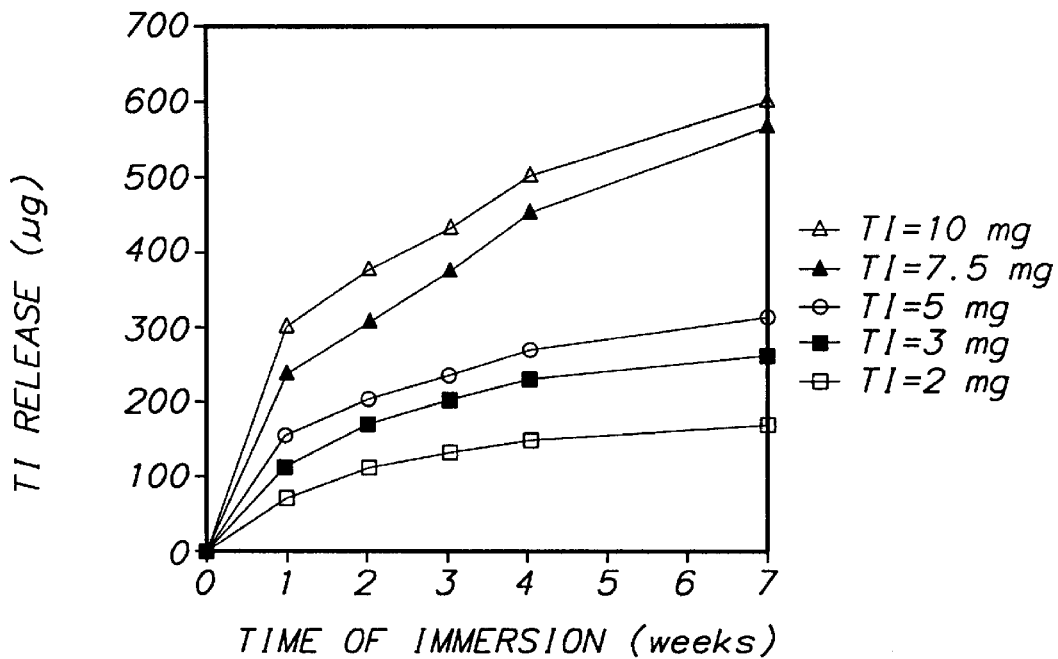
FIGS. 7$a$ and $b$ depict the relationship between trypsin inhibitor concentration and release through 7 weeks and 4 weeks, respectively.
Figure 7B:
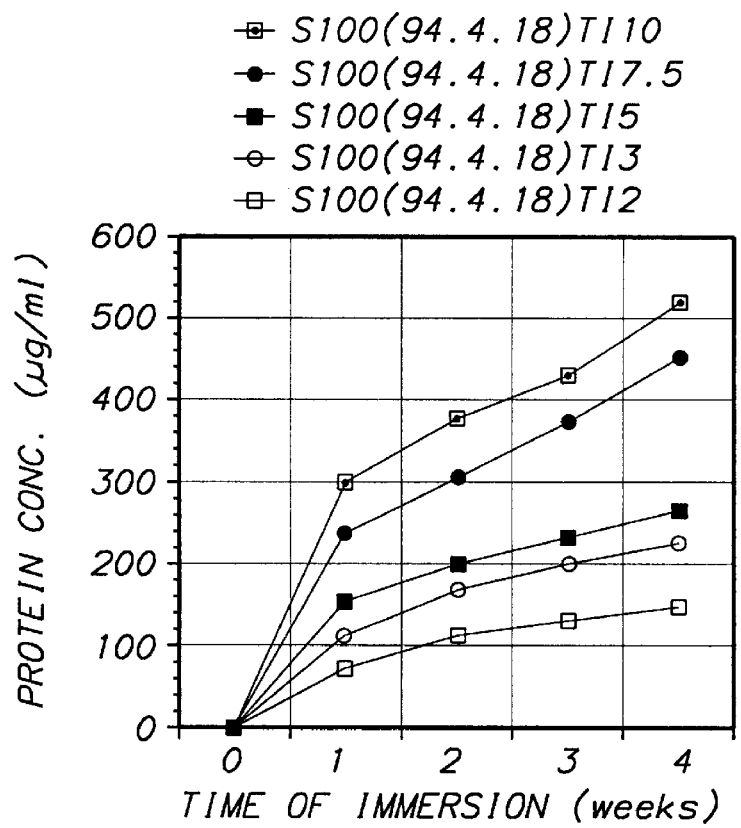

The protein release kinetics of the samples and results listed in Table II are depicted in FIG. 7b. Protein release was measured for a period of four weeks. "T12" (open squares) represents TI=2 from the table. "T13" (open circles) represents TI=3 from the table. "T15" (filled squares) represents TI=5 and T17.5 (filled circles) represents TI=7.5. "TI 10" (filled square within open square) represents TI=10 sample S100 (94.4.18). All samples were in the form of granules having a diameter less than about 2 mm.

As can be seen from FIG. 7a, trypsin inhibitor was continually released from all samples for a period of at least seven (7) weeks.

EXAMPLE 7

Bioactivity of Pure Silica Glass

Sol-gel derived glass with a composition of 100% silica and water/TMOS molar ratio of 15:1 was synthesized and its bioactivity tested in vitro in SPS by measuring changes in calcium-ion concentration. A 5 gram sample was made by combining 12.38 ml of TMOS with 8.87 ml of DI water and sonicating for 5 minutes in an ice cooled bath. To this mixture, 8.87 ml of 0.1N Acetic Acid was added and the mixture sonicated for an additional 15 minutes. Then, 4.43 ml sodium phosphate (0.01M, pH 7) buffer was added and the mixture sonicated for one minute. The liquid sol was cast as 3 ml samples. The pH of the sol as cast was 4.5. The gelling time was approximately 2 hours. Aging of the samples was done at room temperature, for 1 day. Samples were dried for 3 days at 37° C. and weighed about 500 mg.

Samples in the form of discs approximately 1 cm in diameter and 4 mm high (1.76 cm$^2$ SA) were then immersed into SPS (17.6 ml) for a sample surface area to immersion solution volume ratio of 0.1 cm$^{-1}$. Samples were immersed for two weeks with constant stirring at 37° C. SPS concentration of calcium normally averages 100 ppm. After 2 weeks of immersion of samples, the average concentration of calcium in the retrieved SPS averaged 25 ppm. This indicates that calcium was consumed by the glass from solution, most likely by forming a calcium phosphate layer on its surface.

EXAMPLE 8

Bioactivity of Silica-Based Glass Containing Other Oxides

Sol-gel samples with a composition of 65% $SiO_2$, 30% CaO and 5% $P_2O_5$, by weight, were made by combining 1.61 ml TMOS, 5.04 ml 20% calcium methoxyethoxide solution in methoxyethanol, and 0.12 ml triethyl phosphate, and magnetically stirring for 5 minutes at 4° C. To this mixture, 1 ml 1N HCl was added to mimick the conditions for incorporation of proteins, and stirred for an additional minute, for a water/TMOS molar ratio of 5.13. Four, 1 ml samples were cast and the sol gelled in about 5 minutes. These samples were aged for 3 days, and then dried for 4 days at room temperature. Samples after drying weighed about 600 mg.

Figure 2:
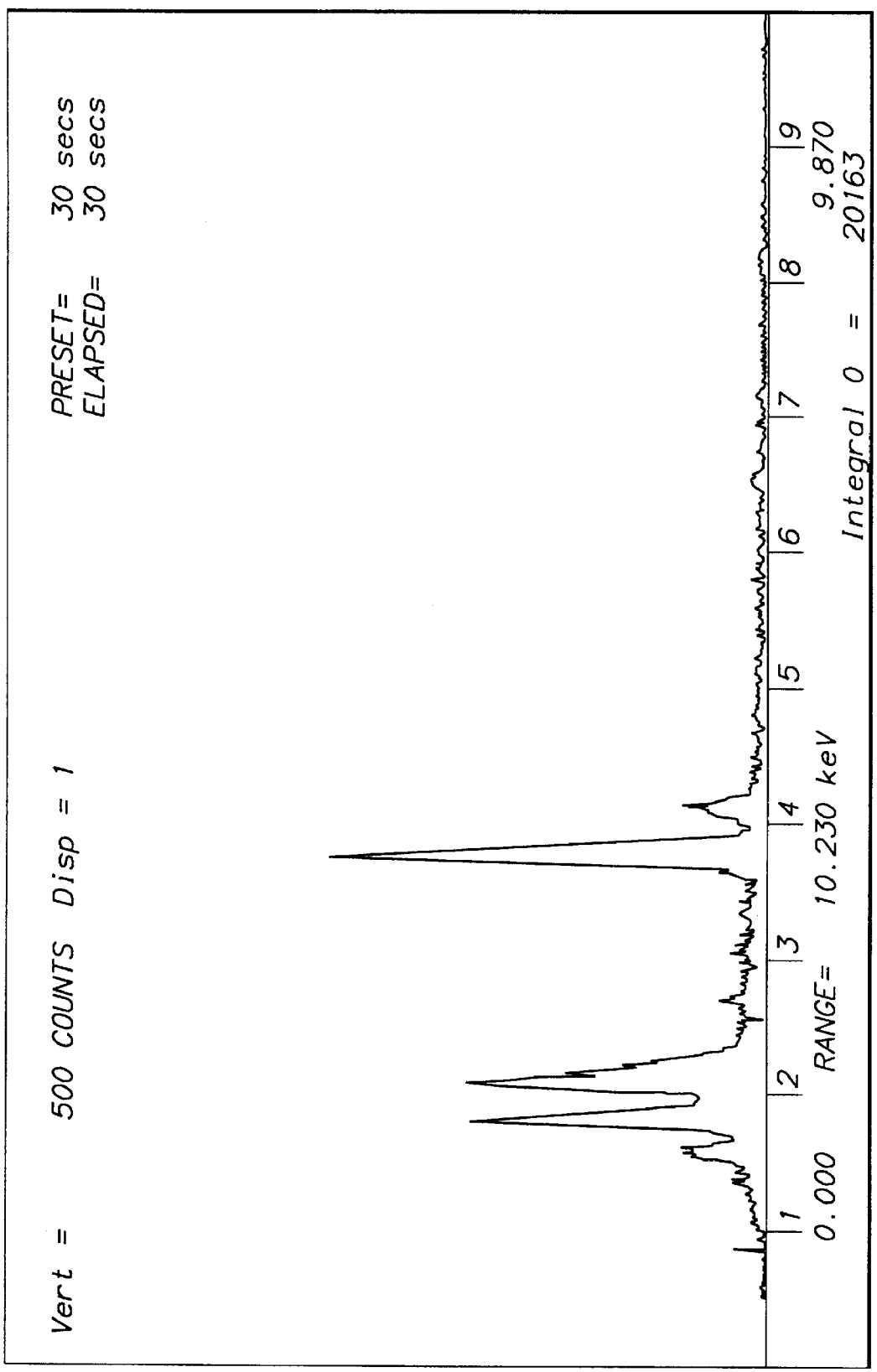
FIG. 2 depicts energy dispersive x-ray analysis of a nodule detected on silica-based glass immersed in simulated physiological solution.

Sol-gel samples were then immersed into 12 ml of SPS to test for calcium phosphate surface layer formation. Samples were retrieved after being immersed 5 days in SPS with constant stirring at 37° C. The samples were viewed using scanning electron microscopy (SEM) and surface analysis was performed using energy dispersive x-ray analysis (EDXA). The surface of the samples contained nodules 1–3 $\mu$m in diameter (FIG. 1) that, when analyzed with EDXA (FIG. 2), contained high proportions of calcium and phosphorous. This indicates the formation of calcium phosphate nucleation sites as a precursor to calcium phosphate layer formation.

EXAMPLE 9

Synthesis of Sol-Gel/TGF-$\beta$ Composite

Recombinant human transforming growth factor beta (TGF-$\beta$1) was incorporated into pure silica sol-gel glass. The sol-gel was synthesized by combining 5 ml TMOS with 5.4 ml of water, for a water/TMOS molar ratio of 9:1, and magnetically stirring for 5 minutes at room temperature. 10 $\mu$L of 1N HCl was added to the mixture and the sol was stirred for 30 minutes. Then, 0.9 ml of the sol was cast into a polystyrene container and 0.1 ml of TGF-$\beta$ solution with 1% bovine serum albumin (BSA) to prevent non-specific binding of the growth factor to the casting container was added. Different quantities of TGF-$\beta$ were added to each sample cast ranging from 0.5 $\mu$g to 2 $\mu$g of TGF-$\beta$ for each solution added with 1% BSA. Samples were aged for 3 days at 37° C. and dried at 37° C. until they had lost approximately 50% of their "as cast" weight.

EXAMPLE 10

TGF-$\beta$1 Release

Sol-gel derived silica glass was synthesized by mixing and stirring TMOS, DI water, and 1N HCl in a molar ratio of 1:10:0.001. Then, 0.9 ml of the sol was cast into 15 ml diameter polystyrene vials and 0.1 ml of a solution containing either 0.5 or 1 $\mu$g of TGF-$\beta$1 was added to the sol samples. TGF-$\beta$1 (Celtrix Lab., Inc.) was prepared according to instructions supplied. Briefly, aliquots from a 2.347 $\mu$g/$\mu$l TGF-$\beta$1 stock solution were resuspended in 10 mM HCl following lyophilization in 1% bovine serum albumin (BSA) (Sigma Chemical Co.). The resulting TGF-$\beta$1 solutions were stored in 1.5 ml microcentrifuge tubes (U.S.A Scientific) at −70° C. until use. The pH of the sols at the time of casting was measured to be 1.7. The vials were sealed and the sols were allowed to gel (15 hours) and age (24 hours) in an incubator at 37° C. Then, the gels were dried to either 50 or 70% weight loss resulting in transparent glass disks about 10 mm in diameter. Part of the samples of each group was crushed to produce granules in a size range from about 500 to about 1000 $\mu$m. A total of 4 sets of silica glass/TGF-$\beta$1 composites were prepared as follows: 1 $\mu$g dose: disks and particles dried to 50% weight loss, and particles dried to 70% weight loss; 0.5 $\mu$g dose: particles dried to 50% weight loss. An additional six silica glass disks containing 0.54 $\mu$g TGF-$\beta$1 and two controls (without TGF-$\beta$1) were prepared and dried to 57% weight loss. The disks had uniform dimensions with an average diameter of 10.17 mm and an average height of 4.93 mm.

The release of TGF-$\beta$1 from the sol-gel derived silica glass particles and disks was measured by immersion in 1 ml of sterile phosphate buffered saline (PBS) containing 1% BSA. Prior to immersion all the samples were sterilized by UV irradiation. The BSA prevents the non-specific binding of TGF-$\beta$1 to the immersion reservoir. Concentration was determined using an enzyme linked immunosorbent assay (ELISA).

The amount of active TGF-$\beta$1 released from the sol-gel materials was assessed using the Mv1Lu mink lung epithelial cell inhibition assay. This assay determines TGF-$\beta$1 activity based on its inhibition of Mv1Lu cell proliferation as measured by [$^3$H]-thymidine incorporation. Jennings et al., "Comparison of the biological activities of TGF beta 1 and TGF-beta 2: Differential activity in endothelial cells", *J. Cell Physiol.* 137:167–172 1988. Confluent Mv1Lu cells (ATCC) were lifted from tissue culture flasks using Cell Dissociation Solution (Specialty Media) and plated in Corning 24-well polystyrene tissue culture dishes. Cells were plated at a density 4.0×10$^4$ cells/well in 1 ml of Dulbecco's Modified Eagle's Medium (DMEM) supplemented with 1% fetal bovine serum (FBS) (Hyclone) and 50 $\mu$g each of penicillin and streptomycin (Sigma Cell Culture). Dishes were incubated at 37° C. and 5% CO$_2$ for 24 hours to allow the cells to adhere to the bottom of the wells.

Following incubation, the wells were aspirated and treated with media containing TGF-$\beta$1 of known picomolar (pM) concentrations as well as lyophilized 1% BSA in 10 mM HCl to serve as the control. The concentrations ranged from 0.1 pM to 10.0 pM and were added in triplicate. Aliquots from sample solutions, i.e. containing TGF-$\beta$1 released from silica glass upon immersion, were diluted into the same range of concentrations and also added to the cells. The dishes were incubated for additional 24 hours.

After treatment with TGF-$\beta$1 standard and sample solutions, the wells were aspirated and the cells labeled for 2 hours with 1 $\mu$Ci/ml of [$^3$H]-thymidine (NEN Research Products) in 1 ml of tissue culture medium. At the conclusion of the incubation period, the relative levels of radioactivity incorporated into cellular DNA were assessed. Each well was washed with 1 ml of PBS, pH 7.4, followed by 10 minutes of treatment with trichloroacetic acid (TCA) to precipitate all unincorporated [$^3$H]-thymidine. Following TCA precipitation, the cells were washed twice with PBS and solubilized with 2% sodium dodecyl sulfate by shaking at room temperature for 2 hours. Radioisotope incorporation into each sample was determined by liquid scintillation counting of a 200 $\mu$l aliquots in 5 ml of ICN Ecolume scintillation fluid using a Beckman LS1800 Liquid Scintillation Counter. Duplicate counts were performed for each sample.

Figure 8:
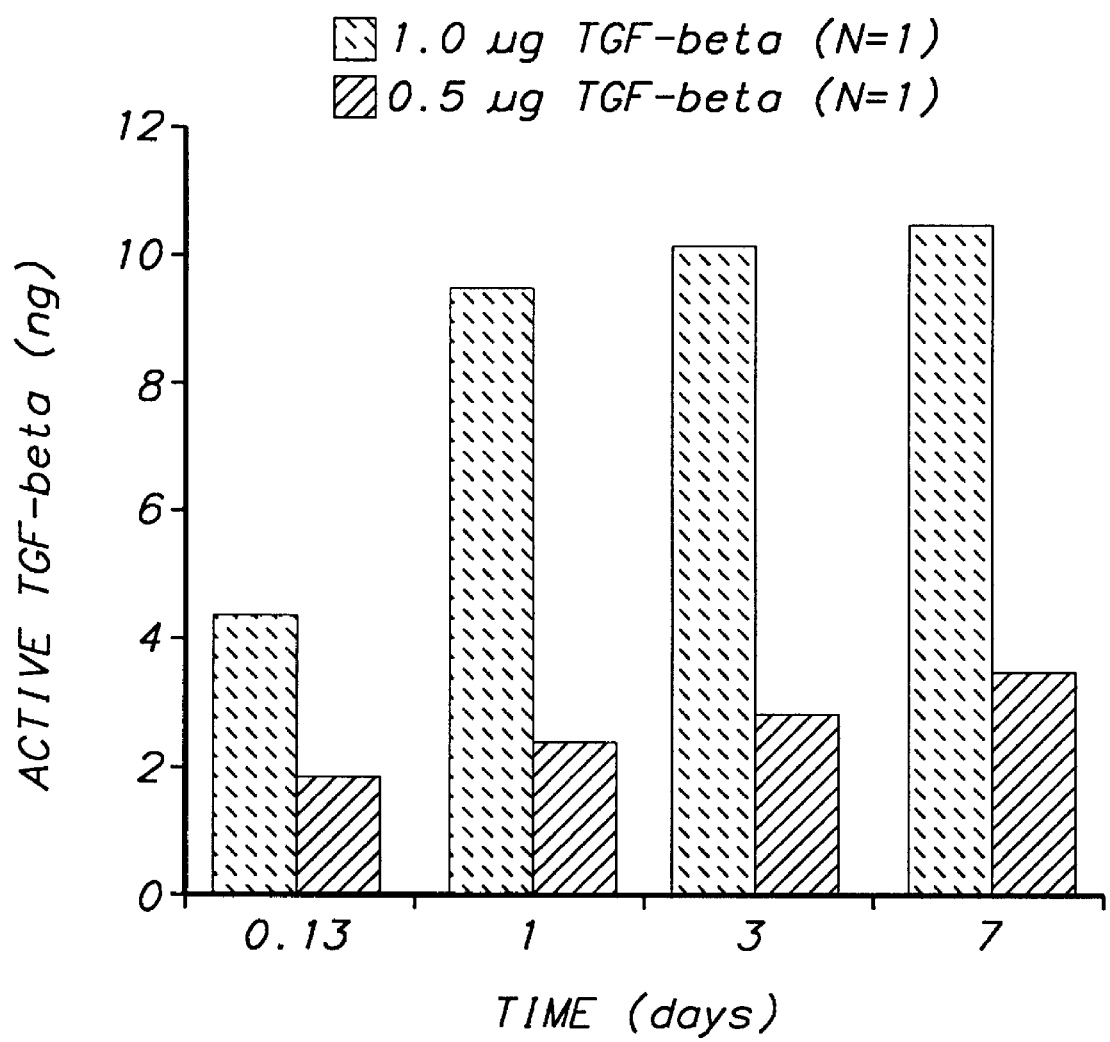
FIG. 8 depicts the effect of incorporated content, 0.5 vs. 1.0 $\mu$g, on the cumulative release of active TGF-$\beta$1 from granules dried to a 50% weight loss.
Figure 9:
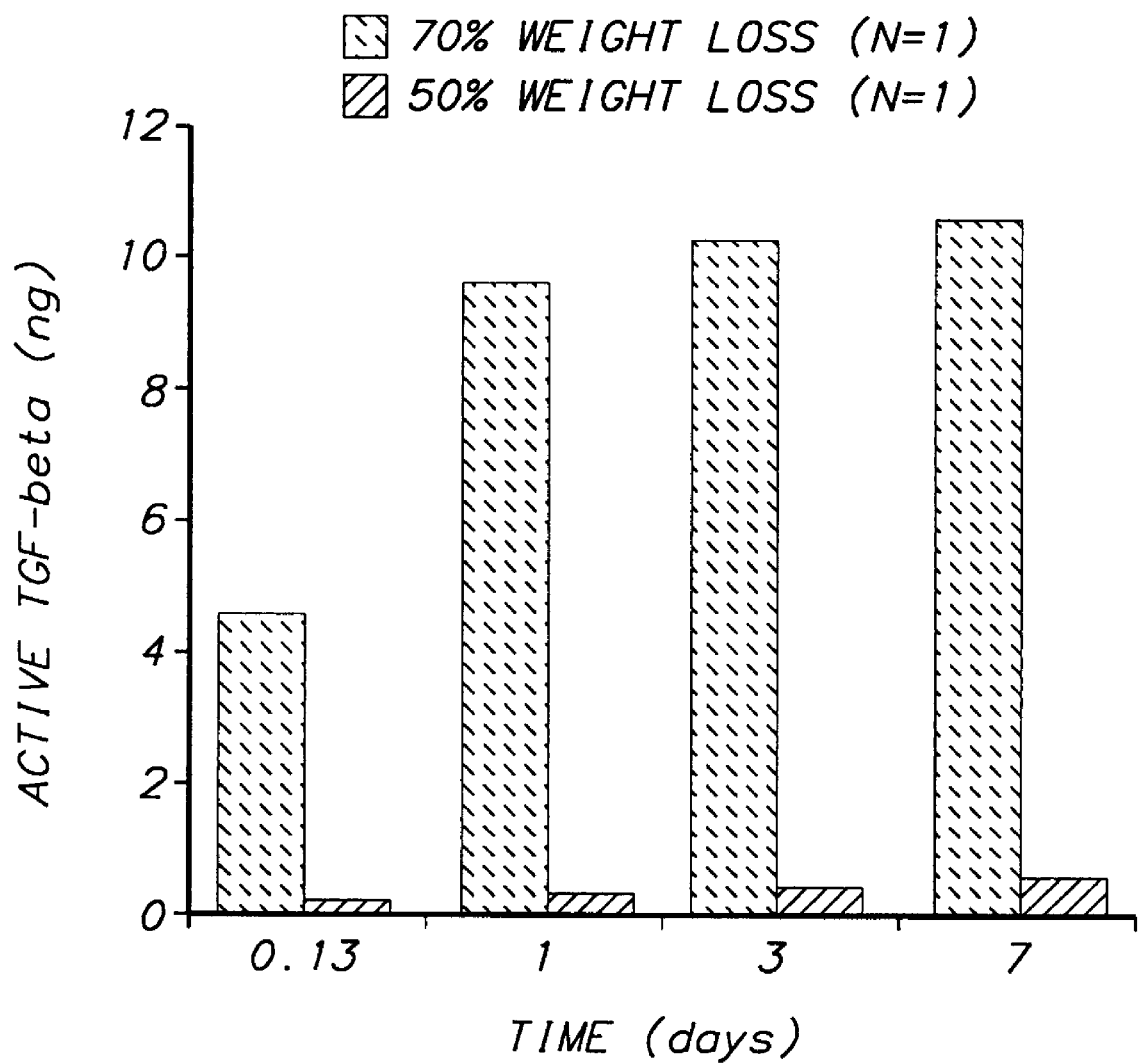
FIG. 9 depicts the effect of the degree of drying, 50 vs. 70% weight loss, from granules loaded with 1.0 $\mu$g TGF-$\beta$1.
Figure 10:
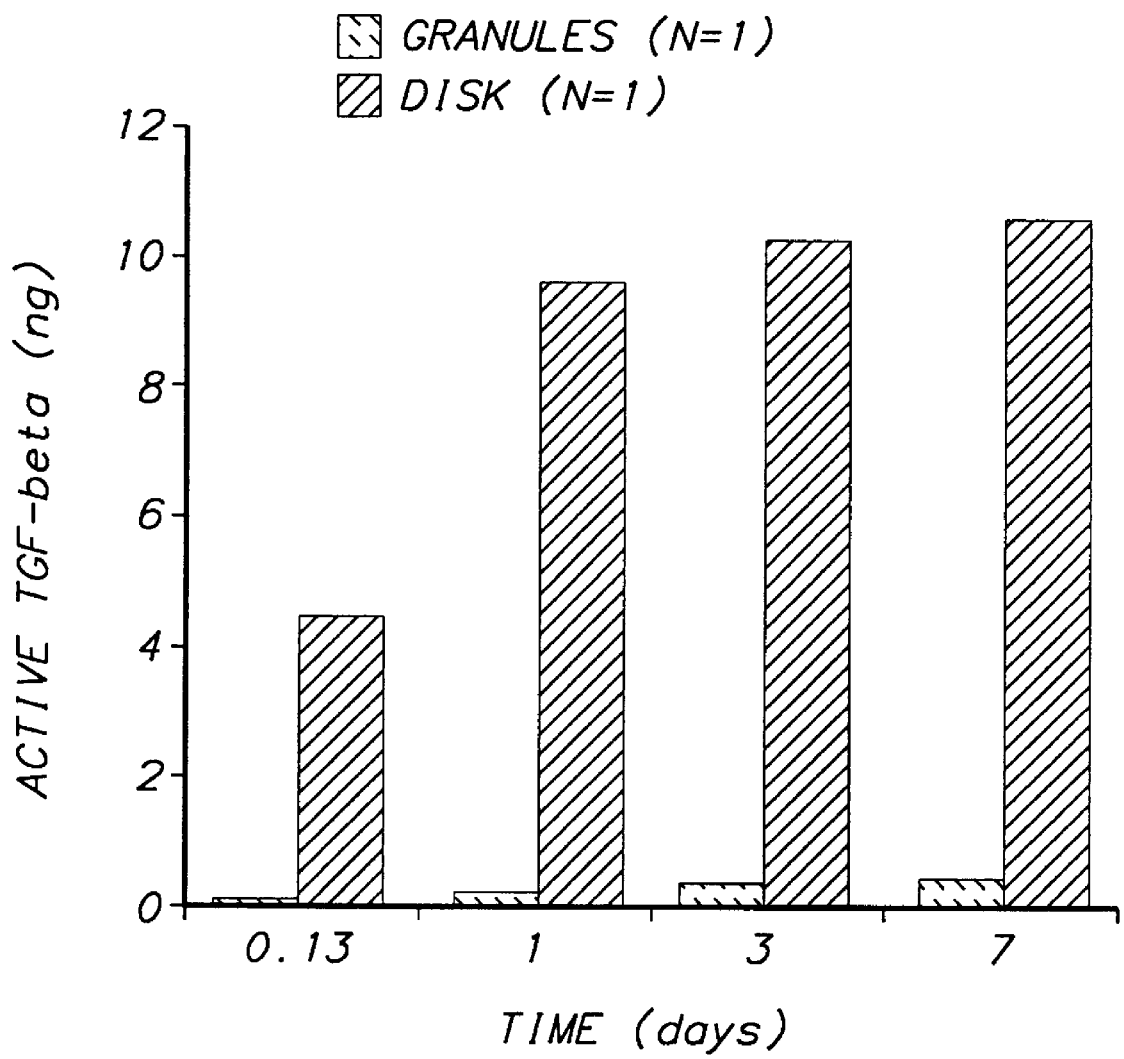
FIG. 10 depicts the effect of SA/V, granules vs. disks, loaded with 1 $\mu$g TGF-$\beta$1 and dried to 50% weight loss.
Figure 11:
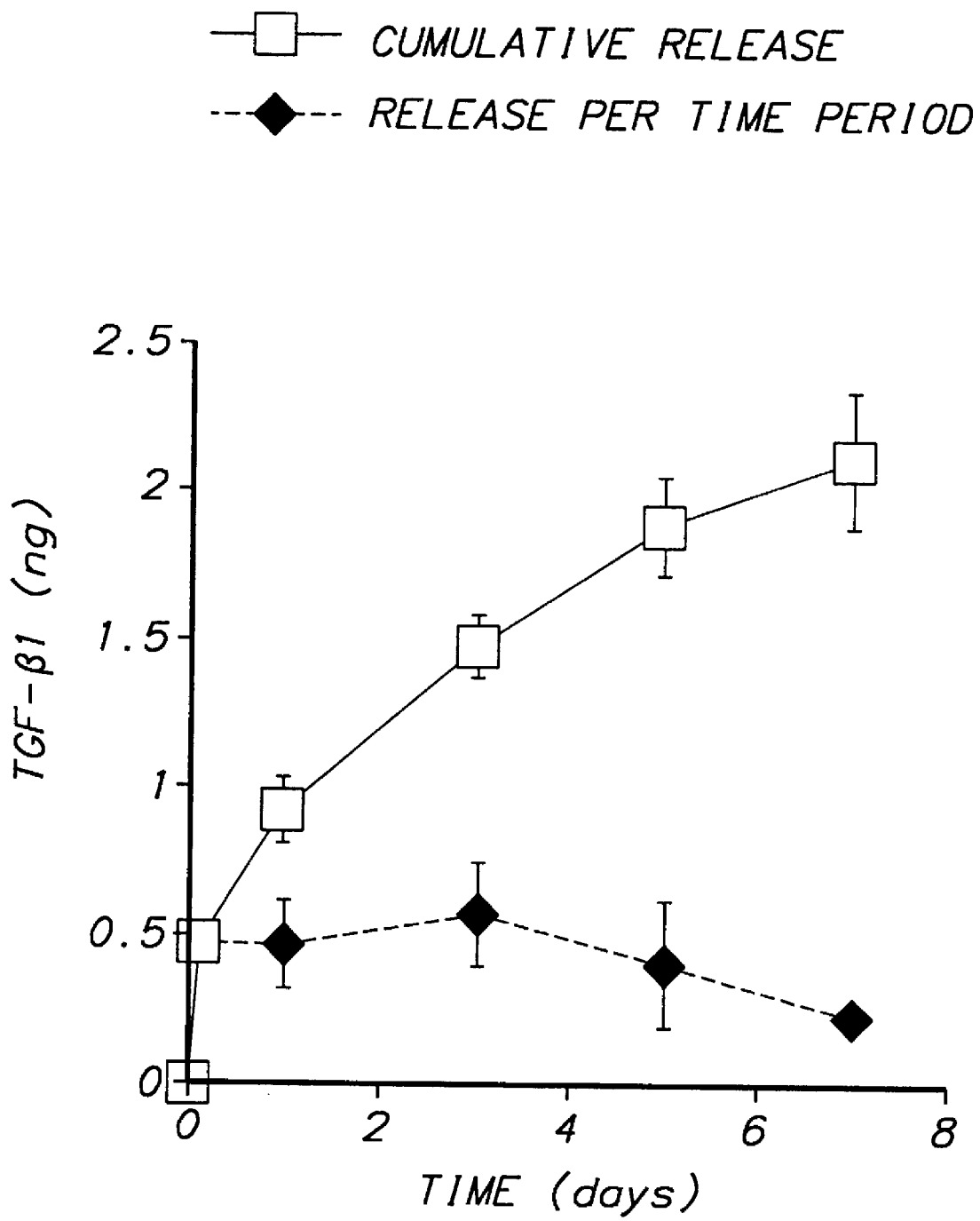
FIG. 11 depicts release of active TGF-$\mu$1, per time period and cumulative, from disks loaded with 0.5$\mu$g and dried to 57% weight loss (n=3).

The effect of various parameters such as the concentration of incorporated TGF-$\beta$1, the degree of drying, and the surface area to volume ratio, on the cumulative release of biologically active TGF-$\beta$1 vs. time is depicted in FIGS. 8, 9, and 10. A sustained release of biologically active TGF-$\beta$1 over a 7 day period, with maximum release occurring at 3 days, was observed for the various group samples. The amount of the released TGF-$\beta$1 depended on the processing parameters. Specifically, the released amount increased with the concentration incorporated and decreased with the degree of drying. The release also depended on the material shape, i.e. SA/V ratio. With an increase in the incorporated content from 0.5 to 1 $\mu$g the amount released from granules increased from 3.4 to 10.5 ng after 7 days of immersion (FIG. 8). The cumulative release also increased significantly with a reduction in a degree of drying from 70 to 50% (FIG. 9). Moreover, the release from small granules was 3 times greater than that from disks due to a significant increase in the SA/V ratio from 1.1 to 10 $mm^{-1}$ (FIG. 10). Thus, among the experimental groups the largest released amount of 10.5 ng, equal to 1% of the incorporated amount, was observed in the case of samples loaded with 1.0 $\mu$g TGF-$\beta$1, dried to 50% weight loss, and crushed to granules in a size range from 500 to 1000 $\mu$m. The measurements, conducted in triplicate, confirmed a sustained release of biologically active TGF-$\beta$1 over 7 days of immersion (FIG. 11).

The sol-gel technology used to synthesize glass/TGF-$\beta$1 composites does not alter the biological functionality of TGF-$\beta$1 The carriers showed a sustained release of therapeutic quantities of the osteoinductive growth factor in its biologically active form.

EXAMPLE 11

Synthesis and Characterization of Ca and P Containing Glasses

A sol-gel derived silica-based glass containing Ca and P was synthesized by mixing the three alkoxides TMOS, CME, and TEP under an argon atmosphere and stirring the mixture for 5 minutes using a magnetic stirrer. A glass having a final composition of about 70% $SiO_2$, 15% CaO, and 5% $P_2O_5$ (percent dry weight) was prepared by mixing 3,47 ml TMOS, 8.4 ml CME, and 0.24 ml TEP. Then, 1.1 ml of the sol was cast per 15 mm diameter polystyrene vial and 0.38 ml of 0.1N acetic acid was added to each of the sols to mimic the conditions for incorporation of proteins. The gels were sealed, aged for three days at room temperature, and dried at 37° C. to 50% weight loss.

Figure 12:
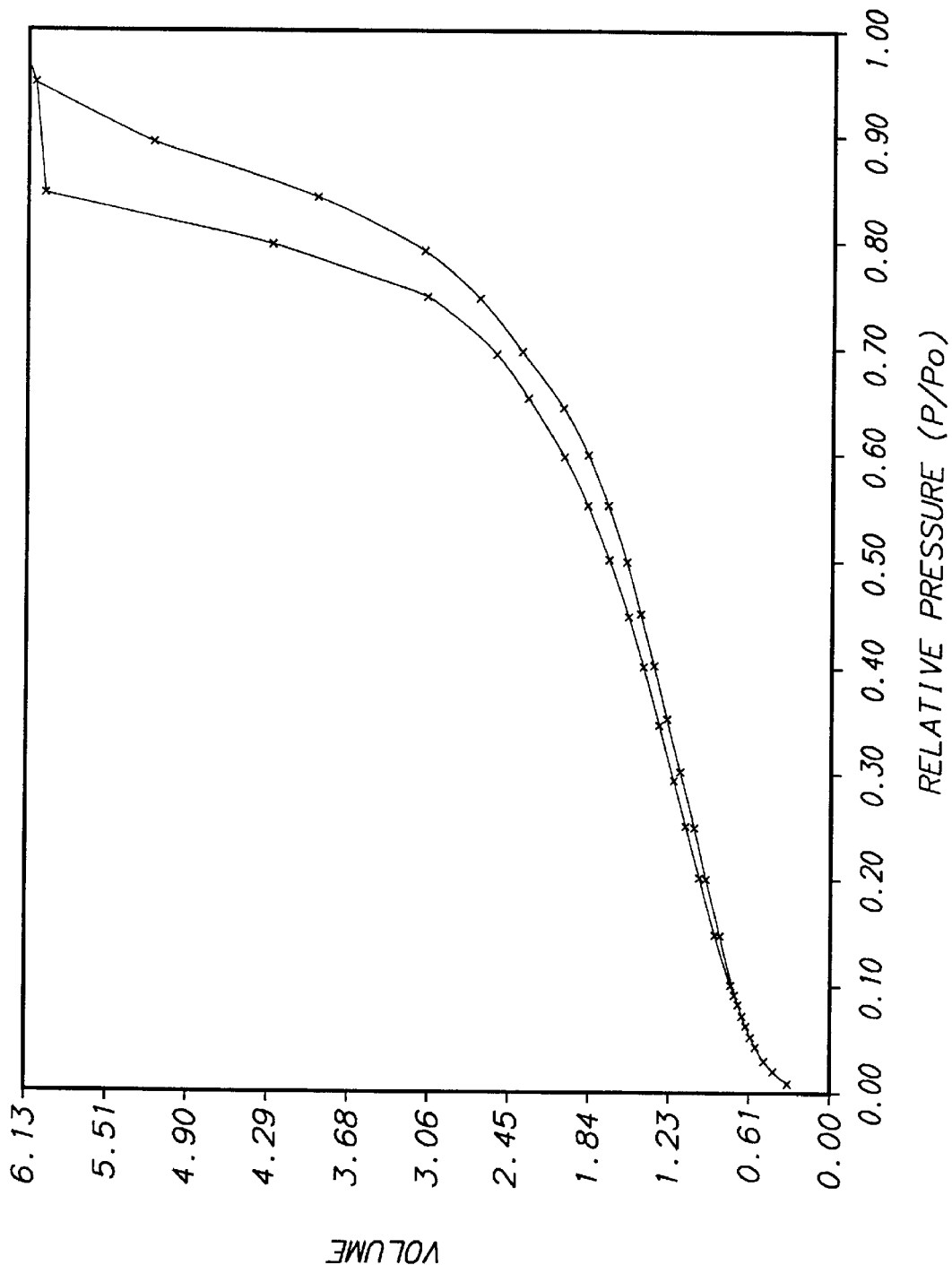
FIG. 12 depicts an absorption isotherm of silica-based glass containing other oxides.

The microstructure of the Ca-P containing silica-based glass prepared was characterized using surface area analysis (Autosorb-1, Quantachrome). Prior to the analysis, the samples were outgassed at 30° C. The material pore structure can be characterized by the shape of absorption isotherms, i.e. plots representing changes in the absorbed gas ($N_2$) volume vs. relative pressure $P/P_0$. The isotherm for the Ca-P containing silica-based glass is depicted in FIG. 12. The shape of the isotherm is characteristic of a mesoporous material, as defined in the *Manual on Using a Surface Analyzer Autosorb*1, Quantachrome Corp., pp. II-4–46, 1992, incorporated herein by reference. Mesoporous materials are defined therein as materials having an intermediate pore size, or pores in the size range of greater than 20 angstroms and less than 500 angstroms. SSA, PV, and mean pore size were determined to be 331 $m^2/g$, 0.97 cc/g, and 58.4 angstroms, respectively.

Figure 13:
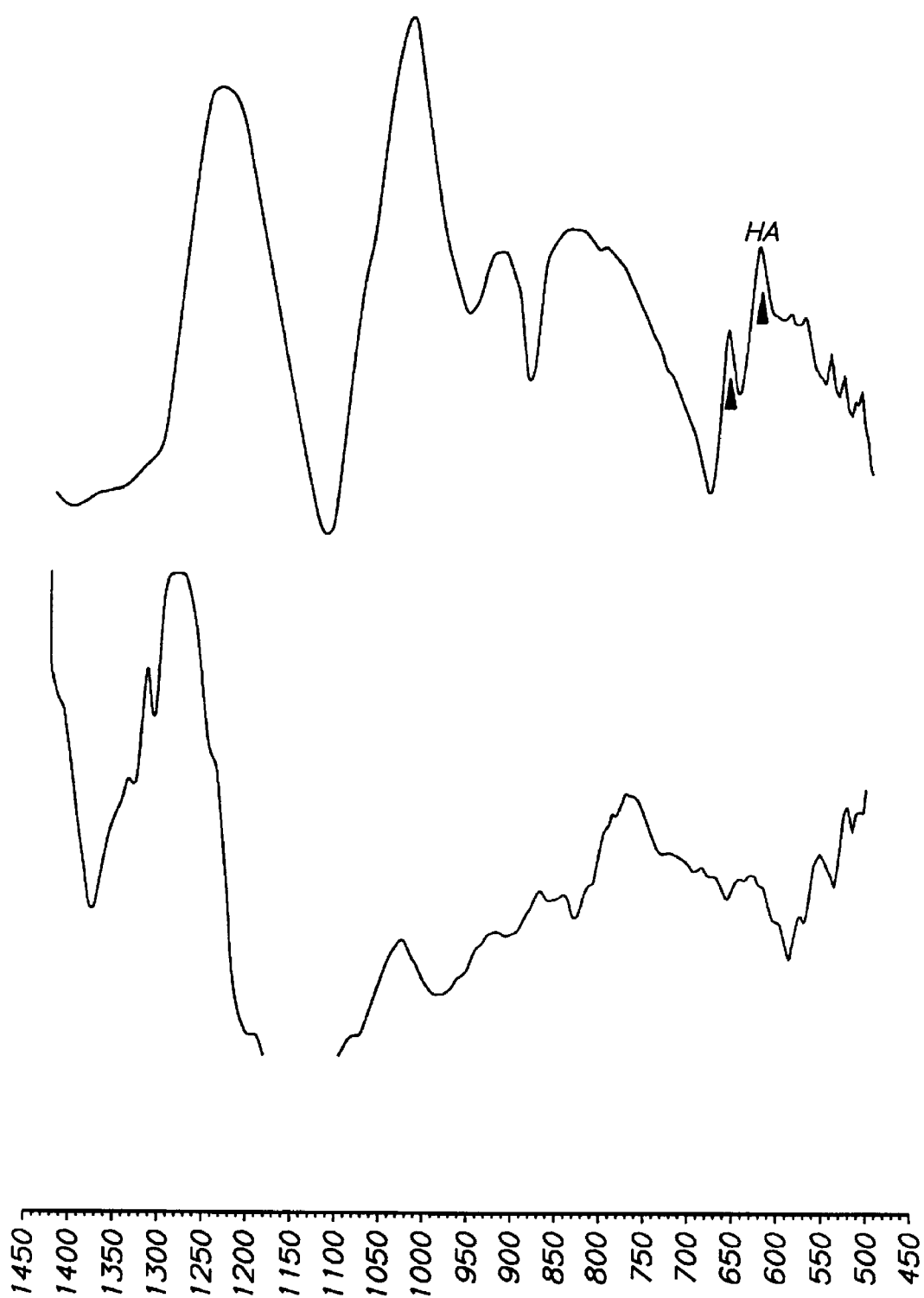
FIG. 13 depicts FTIR spectra of silica-based glass containing other oxides before (lower spectrum) and after (upper spectrum) immersion in SPS.

The ability of the synthesized Ca-P containing glass to form a surface HA layer was assayed after immersion in SPS for one week. The samples were analyzed prior to and after immersion using FTIR. The FTIR spectra of the samples before and after one week of immersion are presented in FIG. 13. The absorption bands in the spectrum before immersion (bottom spectrum) are characteristic of silica-gel. After immersion, a doublet of bands appeared at 603 and 580 $cm^{-1}$ (upper spectrum). These bands indicate the formation of HA on the glass surface, thereby indicating bioactive behavior.

EXAMPLE 12

Synthesis of Ca and P containing Sol-Gel TI Composite

Sol-gel derived glass containing Si, Ca, and P was synthesized by combining TMOS (3.47 ml), CME (8.40 ml) and TEP (0.24 ml), to produce a composition of 70% $SiO_2$, 25% CaO and 5% $P_2O_5$, under an argon atmosphere and mixing for 15 minutes. For each sample, 0.75 ml of the alkoxide mixture was cast in a polystyrene container and then mixed by vortexing with 0.25 ml of 0.1N Acetic acid/protein solution (TI concentration=2, 3, 4, 5 mg). The water/TMOS ratio was 10:1 and the gelling of all the samples occurred in under 1 minute. Aging took place over 3 days in sealed containers at room temperature. The samples were dried to 50% of their as-cast weight at 37° C. by uncapping their containers. After drying, the samples were crushed to produce granules in a size range of about 100–1000 $\mu$m in diameter.

EXAMPLE 13

Trypsin Inhibitor Release

Figure 14:
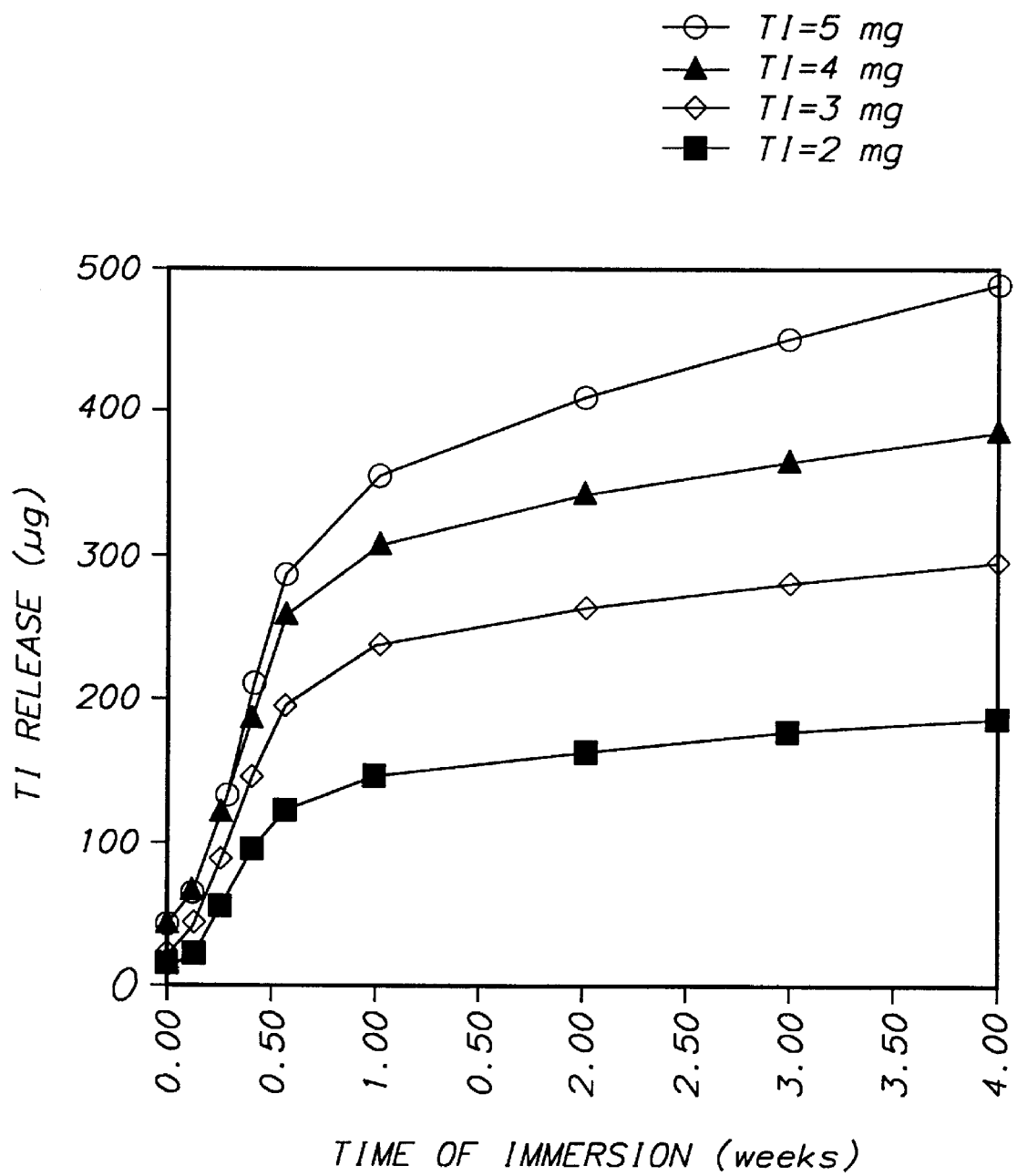
FIG. 14 depicts the release of trypsin inhibitor from sol-gels containing Ca and P.

Protein release studies were performed by immersing 500 mg of the granules in 1 ml of 50 mM tris buffer solution (pH 7.3 at 37° C.). Solutions were replaced completely after each time point varying from 1 hour to seven weeks. Samples were immersed in 1 ml plain tris solution at 37° C. with constant shaking. For each time point measured (1 hr, 2 hrs, 4 hrs, 24 hrs, 48 hrs, 72 hrs, 96 hrs, 1 week, 2 wks, 3 wks, and 4 wks) the solution was exchanged for fresh tris solution and the protein concentrations were measured using a colloidal gold assay. The protein concentrations in the solutions were measured using a gold colloidal assay (Integrated Separation Systems, Natick Mass.). Cumulative protein release from the Ca-P containing glass is represented in FIG. 14.

A comparison with FIG. 7 reveals that a sustained release over long immersion time periods was observed for both types of glass compositions. In both cases, a somewhat rapid release was observed up to immersion times between 4 and 7 days, after which a more gradual release was observed. The released amount depends on the TI concentration incorporated, i.e. with a greater TI content in the glass matrix, the amount released was greater. A 10% release from the silica glass matrix was measured after 6 weeks of immersion, while a 5% release from the Ca-P containing glass was obtained after 4 weeks of immersion. The addition of Ca and P to the sol-gel derived silica glass did not significantly affect the TI release profile and the released amount.

EXAMPLE 14

Bioactivity Studies Including Sol-Gels with Trypsin Inhibitor

Samples were synthesized in a similar way as described in Example 12 above, except that the proportion of alkoxides was changed to achieve three different compositions:

(1) 70% $SiO_2$, 25% CaO and 5% $P_2O_5$
(2) 87% $SiO_2$, 10% CaO and 3% $P_2O_5$
(3) 94% $SiO_2$, 5% CaO and 1% $P_2O_5$ Composition (1) was synthesized both with and without 4 mg of TI, the two other compositions were synthesized without TI. The samples were immersed as 25 mg of granules into 25 ml of SPS solution (a tris buffered solution with electrolyte concentrations similar to plasma) at 37° C. with constant shaking. At the end of the immersion period (either 1, 3, or 7 days) the SPS solution was pipetted out and then analyzed for Ca and $PO_4$ using atomic absorption spectrometry and colorimetry. The granules after immersion were analyzed after immersion using FTIR for the presence of P—O bend peaks at around 600 $cm^{-1}$.

Figure 15:
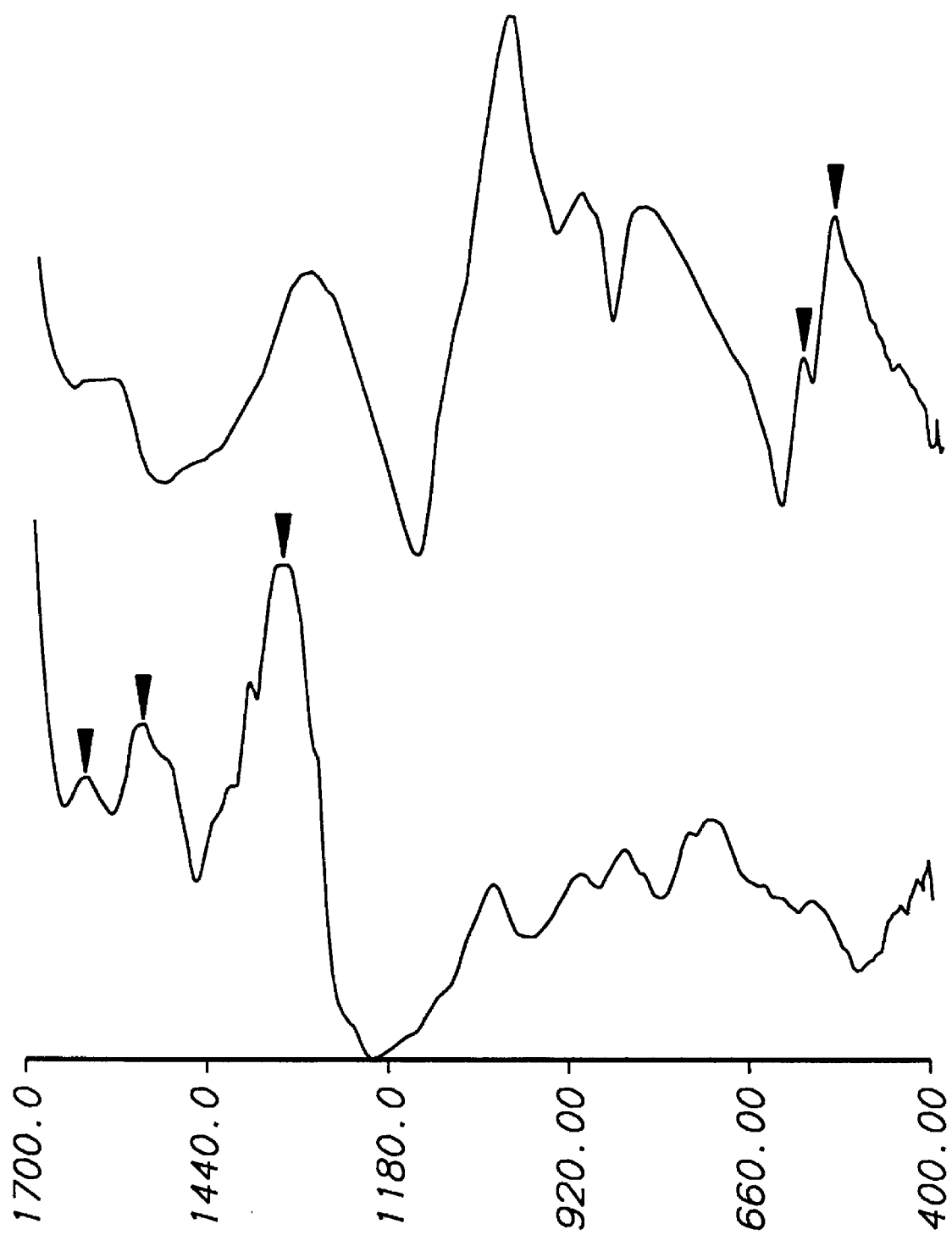
FIG. 15 is an FTIR spectrum of a Ca-P sol-gel containing trypsin inhibitor before and after immersion in a tris buffered electrolyte solution.

The FTIR spectra of glass of composition (1) prior to and after immersion in SPS for one week are represented in FIG. 15. The spectrum of the sample prior to immersion (lower spectrum) shows absorption bands of silica and proteins in the lower (below 1200 $cm^{-1}$) and higher (above 1200 $cm^{-1}$) energy regions, respectively. A doublet of bands, located at 562 and 603 $cm^{-1}$, appeared in the spectrum after immersion (upper spectrum). The doublet, characteristic of the P—O bending mode of vibration, indicates formation of a hydroxyapatite (HA) layer on the surface of sol-gel derived glass. Formation of the HA layer was also detected on the glass of composition (1) without TI. Compositions (2) and (3) also showed formation of the HA layer.

The foregoing examples are meant to illustrate the invention and not to limit it in any way. Those skilled in the art will recognize that modifications can be made which are within the spirit and scope of the invention as set forth in the appended claims.

All references cited herein are incorporated herein by reference.

What is claimed is:

1. A material for filling bony defects comprising an implant and a coating on at least a portion of said implant, said coating comprising a controlled release carrier, said carrier comprising a silica-based glass having a porous matrix and biologically active molecules incorporated throughout said matrix wherein said carrier is prepared using a sol-gel derived process, and said biologically active molecules are incorporated during the liquid phase of the sol, at a temperature of about 40° C. or below.

2. The material of claim 1 wherein said implant consists of bioactive glass.

3. The material of claim 2 wherein said bioactive glass is in granular form.

4. The material of claim 1 wherein said implant comprises a prosthetic device.

* * * * *